United States Patent [19]

DeLuca et al.

[11] Patent Number: 5,414,098

[45] Date of Patent: May 9, 1995

[54] HOMOLOGATED VITAMIN $D_2$ COMPOUNDS AND THE CORRESPONDING 1α-HYDROXYLATED DERIVATIVES

[75] Inventors: Hector F. DeLuca, Deerfield; Heinrich K. Schnoes; Kato L. Perlman, both of Madison, all of Wis.

[73] Assignee: Wisconsin Alumni Research Foundation, Madison, Wis.

[21] Appl. No.: 985,432

[22] Filed: Dec. 3, 1992

Related U.S. Application Data

[60] Continuation of Ser. No. 732,008, Jul. 22, 1991, abandoned, which is a division of Ser. No. 654,746, Feb. 13, 1991, Pat. No. 5,260,290, which is a continuation-in-part of Ser. No. 481,990, Feb. 14, 1990, Pat. No. 5,030,772.

[51] Int. Cl.$^6$ .......................................... C07C 401/00
[52] U.S. Cl. .................................................. 552/653
[58] Field of Search .......................... 552/653; 514/167

[56] References Cited

U.S. PATENT DOCUMENTS

| | | |
|---|---|---|
| 3,585,221 | 6/1971 | DeLuca . |
| 3,880,894 | 4/1975 | DeLuca et al. . |
| 3,907,843 | 9/1975 | DeLuca et al. . |
| 4,004,003 | 1/1977 | Babcock et al. ............. 514/167 |
| 4,230,701 | 10/1980 | Holick et al. ............. 514/167 |
| 4,338,250 | 7/1982 | DeLuca et al. ............. 552/653 |
| 4,448,721 | 5/1984 | DeLuca et al. ............. 552/653 |
| 4,508,651 | 4/1985 | Baggiolini et al. ............. 552/653 |
| 4,758,383 | 7/1988 | Tachibana ............. 552/653 |
| 4,769,181 | 9/1988 | DeLuca et al. ............. 552/653 |
| 4,847,012 | 7/1989 | DeLuca et al. ............. 552/653 |
| 4,866,048 | 9/1989 | Calverley et al. ............. 514/167 |
| 4,929,609 | 5/1990 | Batcho et al. ............. 514/167 |
| 4,973,584 | 11/1990 | DeLuca et al. . |

FOREIGN PATENT DOCUMENTS

| | | |
|---|---|---|
| 0386793 | 9/1990 | European Pat. Off. . |
| 0402982 | 12/1990 | European Pat. Off. . |
| 0421561 | 4/1991 | European Pat. Off. . |
| 2554444 | 5/1985 | France . |
| 2139627 | 11/1984 | United Kingdom . |
| 2217716 | 11/1989 | United Kingdom . |
| 8503939 | 9/1985 | WIPO . |
| 8505622 | 12/1985 | WIPO . |
| 8602078 | 4/1986 | WIPO . |
| 8604333 | 7/1986 | WIPO . |
| 8910351 | 11/1989 | WIPO . |
| 8910352 | 11/1989 | WIPO . |
| 9100271 | 1/1991 | WIPO . |

OTHER PUBLICATIONS

Chemical and Pharmaceutical Bulletin, vol. 34, No. 11, Nov. 1986, The Pharmaceutical Society of Japan, H. Sai et al.: "Synthesis of some side-chain homologues of 1alpha; 25-dihydroxyvitamin $D_3$ and investigation of their biological activities", pp. 4508–4515.

Chemical Abstracts, vol. 101, No. 15, 8 Oct. 1984, (Columbus, Ohio, US), I. A. Alekseeva et al.: "Activity of 5, 6-trans- and 22-dehydro analogs of 1,25-dihydroxyvitamin $D_3$", see p. 601, abstract 129315q, & Khim.-Farm. Zh. 1984, 18(6), 659–65.

Perlman et al, "24-Homologated 1,25-Dihydroxyvitamin $D_3$ Compounds: Separation of Calcium and Cell Differentiation Activities," Biochemistry, 1990, vol. 29, 190–196.

*Primary Examiner*—Johann Richter
*Assistant Examiner*—Kimberly J. Kestler
*Attorney, Agent, or Firm*—Andrus, Sceales, Starke & Sawall

[57] ABSTRACT

The invention provides new 24, 26, and/or 27 homologated vitamin $D_2$ compounds, such as 26,27-dihomo-1α-hydroxyvitamin $D_2$, 26,27-dihomo-1α-hydroxy-24-epi-vitamin $D_2$, 26,27-dihomo-1α,25-dihydroxy-24-epi-vitamin $D_2$ and certain hydroxy-protected derivatives thereof. The new epi compounds in particular exhibit a distinctive activity pattern comprising high potency in stimulating intestinal calcium transport and little or no activity in inducing bone calcium mobilization or the differentiation of undifferentiated cells in culture, thereby evincing utility in the treatment of diseases characterized by loss of bone mass. In contrast, the natural form exhibits no activity in either mobilizing calcium from bone or stimulating intestinal calcium transport. A process for preparing such compounds is also disclosed.

5 Claims, No Drawings

HOMOLOGATED VITAMIN $D_2$ COMPOUNDS AND THE CORRESPONDING 1α-HYDROXYLATED DERIVATIVES

This application is a continuation of application Ser. No. 07/732,008, filed Jul. 22, 1991, now abandoned, which is a divisional of application Ser. No. 07/654,746, filed Feb. 13, 1991, now U.S. Pat. No. 5,260,290, which is a continuation-in-part of application Ser. No. 07/481,990, filed Feb. 14, 1990, now U.S. Pat. No. 5,030,772.

TECHNICAL FIELD

This invention relates to biologically active vitamin D compounds.

More specifically, this invention relates to novel 24, 26 and/or 27 homologated derivatives of vitamin $D_2$ and the corresponding hydroxylated forms thereof.

BACKGROUND OF THE INVENTION

The D vitamins are very important agents for the control of calcium and phosphate metabolism in animals and humans, and have long been used as dietary supplements and in clinical practice to assure proper bone growth and development. It is now known that the in vivo activity of these vitamins, specifically of vitamin $D_2$ and $D_3$, is dependent on metabolism to hydroxylated forms. Thus, vitamin $D_3$ undergoes two successive hydroxylation reactions in vivo, leading first to 25-hydroxyvitamin $D_3$ and then to 1,25-dihydroxyvitamin $D_3$ and the latter is thought to be the compound responsible for the well-known beneficial effects of vitamin $D_3$. Likewise, vitamin $D_2$, which is commonly used as a dietary supplement, undergoes an analogous hydroxylation sequence to its active forms, being first converted to 25-hydroxyvitamin $D_2$ (25-OH-$D_2$) and then to 1,25-dihydroxyvitamin $D_2$ (1,25-(OH)$_2D_2$). These facts are well established and well known in the art [see, for example, Suda et al. Biochemistry 8, 3515 (1969) and Jones et al. Biochemistry 14, 1250 (1975)].

Like the metabolites of the vitamin $D_3$ series, the hydroxylated forms of vitamin $D_2$ named above are, because of their potency and other beneficial properties, highly desirable dietary supplements, or pharmaceutical agents, for the cure or prevention of bone or related diseases, and their value and possible use is recognized in patents relating to these compounds [U.S. Pat. Nos. 3,585,221 and 3,880,894].

Whereas many metabolites of vitamin $D_3$ have been prepared by chemical synthesis, there has been less work on the preparation of vitamin $D_2$ metabolites. The known synthetic processes for the metabolites of the $D_3$-series (especially as far as they relate to the preparation of side chain hydroxylated compounds) are, of course, in general not suitable for the preparation of the corresponding vitamin $D_2$ metabolites, since the latter are characterized by a side chain structure (i.e. presence of a double bond and an extra methyl group) which requires a different synthetic approach from that applicable to side chain hydroxylated $D_3$ compounds.

Various approaches for the preparation of vitamin $D_2$ metabolites are known, and are described in U.S. Pat. Nos. 4,448,721, 4,847,012 and 4,769,181. Other preparations of 25-OH-$D_2$ and 1α,25-(OH)$_2D_2$ compounds involving condensation of side chains with a steroid nucleus are shown in Yamada et al, "Facile And Stereoselective Synthesis of 25-hydroxyvitamin $D_2$", Tetrahedron Letters, Vol. 25, No. 33, pp. 3347–3350, 1984 and in Tsuji et al, "A New And Convenient Synthesis of 1α,25-Dihydroxyvitamin $D_2$ And Its 24R-Epimer", Bull, Chem. Soc. Jpn., Vol. 62, No. 10, pp. 3132–3137, 1989. Perlman et al have reported the preparation of the epimer of 1α-OH-$D_2$ by condensation of a suitable side chain fragment with a vitamin D nucleus in J. Chem. Soc. Chem. Com. pp. 1113–1115, 1989.

The natural vitamin D-derived hormone, 1α,25-dihydroxyvitamin $D_3$, and its 25-deoxy analog, 1α-hydroxyvitamin $D_3$, both exhibit high activity in vivo, being known as potent stimulators of the intestinal absorption of calcium and the mobilization of calcium from bone and as effective promoters of bone calcification. A very similar activity pattern is shown by 1α,25-dihydroxyvitamin $D_2$ (U.S. Pat. No. 3,880,894) and its 25-deoxy analog, 1α-hydroxyvitamin $D_2$ (U.S. Pat. No. 3,907,843). These compounds likewise elicit the full spectrum of vitamin D-type responses such as intestinal calcium transport, bone mineral mobilization and bone calcification response in the animal or human. Structurally, 1α,25-dihydroxyvitamin $D_2$ and 1α-hydroxyvitamin $D_2$ are characterized by having a C-24 stereochemistry as it occurs in the side chain of ergosterol, i.e. these compounds are defined by the structures shown below, where R represents side chains (a) and (b), respectively:

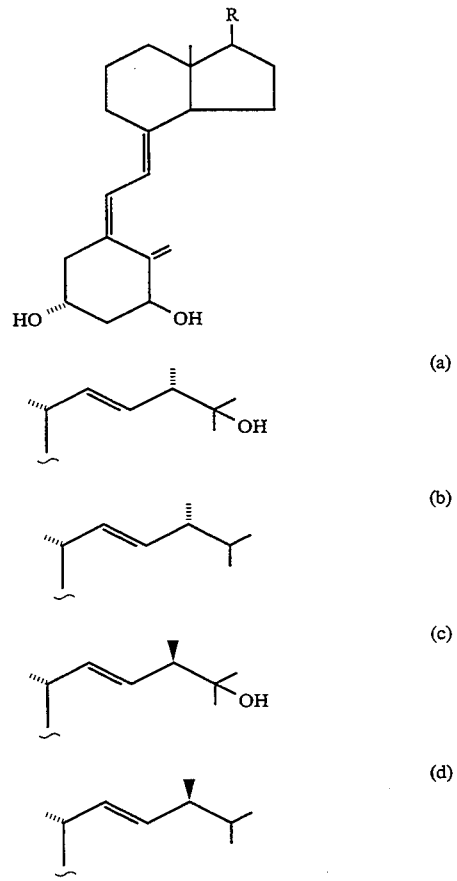

More recently the C-24-epimer of 1α,25-dihydroxyvitamin $D_2$ and 1α-hydroxyvitamin $D_2$ has been prepared and tested. These compounds are characterized by the structures shown above, where R represents side chains (c) and (d) respectively. Remarkably these C-24-epimeric vitamin D derivatives exhibit a distinctly different biological activity in that they promote intestinal calcium absorption and the calcification of bone, but elicit little or no bone calcium mobilization response.

DISCLOSURE OF INVENTION

This invention provides new homologated vitamin $D_2$ analogs which may be represented by the structure below, as well as the 1α-hydroxy-analogs and the protected hydroxy derivatives of the compounds:

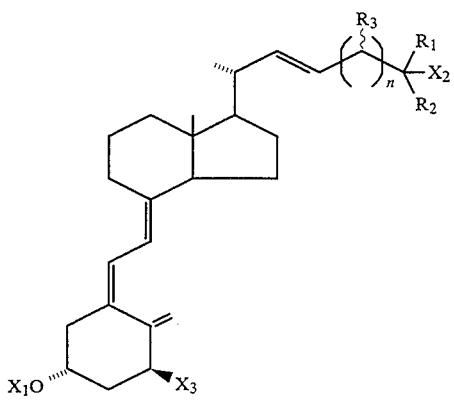

where the configuration about carbon 24 may be R or S and wherein n is an integer having a value of from 1 to 5, $X_1$ is selected from hydrogen or a hydroxy protecting group, $X_2$ is selected from hydrogen, hydroxy, and protected hydroxy, $X_3$ is selected from hydrogen, hydroxy, and protected hydroxy, $R_3$ is selected from alkyl, hydroxy, protected hydroxy, hydrogen or fluorine, and wherein $R_1$ and $R_2$, which may be the same or different, are each selected from an alkyl or aryl group, with the proviso that when $X_1$ is hydrogen, $X_2$ is hydrogen or hydroxy, $X_3$ is hydrogen or hydroxy and n is 1, $R_1$, $R_2$, and $R_3$ cannot all be methyl.

These compounds are distinguished from the previously known 1α-hydroxyvitamin $D_2$ and 1α-hydroxy-24-epi-vitamin $D_2$ compounds by homologation at the 24, 26 and/or 27 positions. Specific compounds disclosed include 26,27-dihomo-1α-hydroxyvitamin $D_2$, 26,27-dihomo-1α,25-dihydroxyvitamin $D_2$, 26,27-dihomo-1α-hydroxy-24-epi-vitamin $D_2$, 26,27-dihomo-1α,25-dihydroxy-24-epi-vitamin $D_2$, and the corresponding 26,27-tetrahomo compounds, as well as 24-dihomo-1α-hydroxy-24-epi-vitamin $D_2$, 24-dihomo-1α,25-dihydroxy-24-epi-vitamin $D_2$, and the corresponding 24-trihomo compounds. It should be noted that with respect to all homologated compounds i.e. whether the compound is 24 and/or 26 and/or 27 homologated, the above-noted structural formula encompasses 25-hydroxylated compounds, 1α-hydroxylated compounds, as well as 1α,25-dihydroxylated compounds.

It should be noted in this description that the term "24-dihomo" refers to the addition of two methylene groups substituted with the group $R_3$ at the carbon 24 position in the side chain (so that n is 3). Likewise, the term "24-trihomo" refers to the addition of three such substituted methylene groups (so that n is 4). Also, the term "26,27-dihomo" refers to the addition of a methyl group at the carbon 26 and 27 positions so that $R_1$ and $R_2$ are ethyl groups. Likewise, the term "26,27-tetrahomo" refers to the addition of an ethyl group at the 26 and 27 positions so that $R_1$ and $R_2$ are propyl groups.

A novel and convenient synthesis of vitamin $D_2$ compounds has now been developed and is also described herein. This synthesis provides homologated vitamin $D_2$ compounds characterized by the structures previously shown as well as non-homologated vitamin $D_2$ compounds shown below where $X_2$ is hydrogen, such as vitamin $D_2$ itself and the 24-epimer of vitamin $D_2$, namely 24-epi-vitamin $D_2$ (24-epi $D_2$), characterized by the structures shown below where $X_1$ and $X_2$ are both hydrogen and $R_1$, $R_2$ and $R_3$ are methyl. This synthesis also provides 25 hydroxylated vitamin $D_2$ compounds, such as 25-hydroxyvitamin $D_2$ (25-OH-$D_2$) and the 24-epimer of 25-hydroxyvitamin $D_2$, namely 25-hydroxy-24-epi-vitamin $D_2$ (25-OH-24-epi $D_2$), characterized by the structures shown below where $X_1$ is hydrogen, $X_2$ is hydroxy and $R_1$, $R_2$ and $R_3$ are methyl.

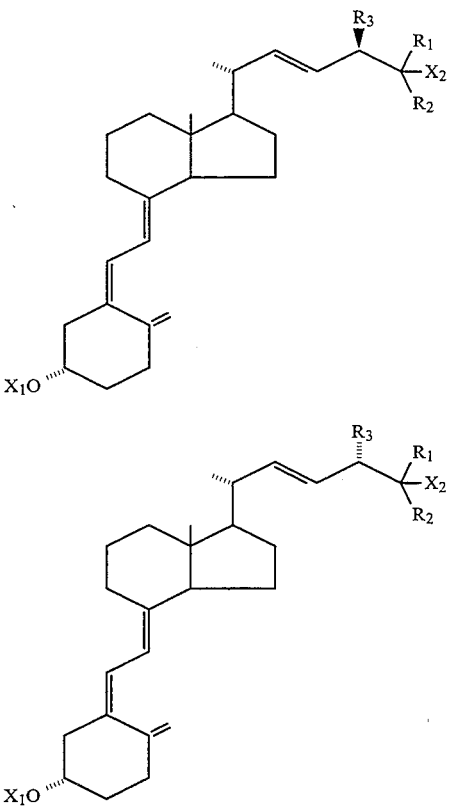

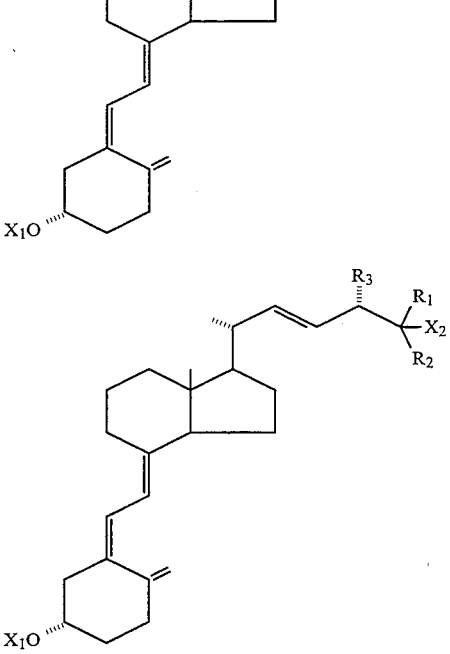

This synthesis thus provides compounds where $X_2$ may be either hydrogen or hydroxy, as well as the corresponding alkyl or aryl analogs thereof, characterized by the structures above where $R_1$ and $R_2$ are alkyl or aryl, and the corresponding side chain substituted derivatives where $R_3$ is alkyl, hydroxy, protected hydroxy (as defined below for $X_1$ and $X_2$), hydrogen or fluorine, and the hydroxy-protected derivatives of these compounds characterized by the structures above, where $X_1$ is selected from the group consisting of acyl, alkylsilyl, or alkoxyalkyl and $X_2$ is selected from the group consisting of O-acyl, O-alkylsilyl, or O-alkoxyalkyl.

In addition, the present process provides the 5,6-trans-isomers of the above compounds, as well as the 24 and/or 26 and/or 27 homologated compounds previously shown herein. Furthermore, the above compounds can be 1α-hydroxylated by known methods, so as to produce the corresponding 1α-hydroxyvitamin D derivatives. Especially preferred examples of the latter are 1α-hydroxyvitamin $D_2$, 1α,25-dihydroxyvitamin $D_2$, 1α-24-epi-vitamin $D_2$ and 1α,25-dihydroxy-24-epi-vitamin $D_2$.

The term "acyl", as used in this specification or in the claims, signifies an aliphatic acyl group of from 1 to about 6 carbons, in all possible isomeric forms (e.g. formyl, acetyl, propionyl, butyryl, isobutyryl, valeryl, etc.), or an aromatic acyl group (aroyl group) such as benzoyl, the isomeric methylbenzoyls, the isomeric nitro- or halo-benzoyls, etc., or a dicarboxylic acyl group of from 2 to 6 atoms chain length, i.e. acyl groups of the type $ROOC(CH_2)_nCO-$, or $ROCCH_2-O-CH_2CO-$, where n has values between 0 and 4 inclusive and R is hydrogen or an alkyl radical, such as oxalyl, malonyl, succinoyl, glutaryl, adipyl, diglycolyl. The term "alkyl" refers to a lower alkyl group of 1 to 6 carbons in all possible isomeric forms, e.g. methyl, ethyl, propyl, isopropyl, butyl, isobutyl, sec.-butyl, pentyl, etc., and the work "aryl" signifies a phenyl or substituted phenyl group, e.g. alkylphenyl, methoxyphenyl, etc. The term "alkylsilyl" refers to trialkyl silicone groupings where the alkyl groups may be the same or different as exemplified by trimethylsilyl, triethylsilyl, dimethyl-tert.-butylsilyl and similar groupings. The term "alkoxyalkyl" refers to protecting groups such as methoxymethyl, ethoxymethyl, methoxyethoxymethyl, and similar alkoxymethyl groups, as well as the related cyclic structures, such as tetrahydropyranyl or tetrahydrofuranyl.

The overall process developed for the preparation of the above compounds may be divided into two general phases, namely (a) addition of a completed, preformed side chain fragment to a suitable steroidal precursor to produce a 5,7-diene steroid as the central intermediate, and (b) conversion of this 5,7-diene to the vitamin D structure to produce the desired vitamin D compound, and, if desired, (c) further conversion of the latter product to the corresponding 1α-hydroxyvitamin D compound. This process avoids the relatively difficult step of isomer separation which is required after conversion in the process of U.S. Pat. No. 4,448,721. The process of the present invention also increases the yield of the end product since it utilizes a completed, preformed pure isomer side chain fragment to make the desired end product, rather than a mixture of side chain isomers as in U.S. Pat. No. 4,448,721.

In general terms, the process of this invention comprises the reaction of a steroidal 22-aldehyde of the structure:

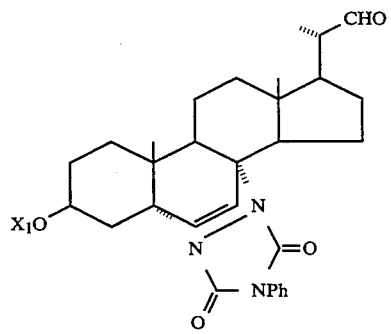

where $X_1$ is hydrogen or a hydroxy-protecting group, with a sulfone derivative of the general formula,

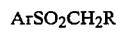

$ArSO_2CH_2R$ where Ar represents a phenyl or tolyl group, and R is selected from the group consisting of straight or branched, substituted or unsubstituted, hydrocarbon radicals of from 1 to 25 carbon atoms, where the substituents are selected from the group consisting of hydroxy, protected hydroxy, and fluorine.

The coupling reaction, conducted in a basic medium, between the above aldehyde and sulfone derivatives, yields a condensation product of the formula:

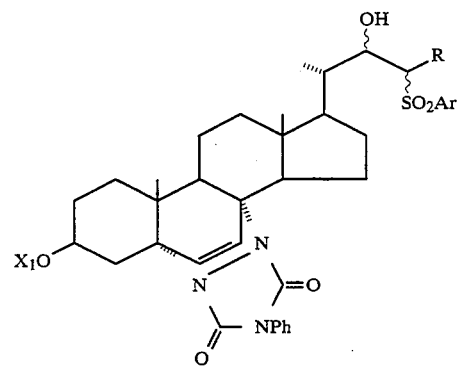

which is then subjected to reduction (either as the 22-hydroxy, or as the corresponding 22-O-acylated derivative) using metal amalgams (Na, Al, Zn amalgams) or related dissolving metal reduction systems, so as to provide the 22, 23-unsaturated steroid of the formula:

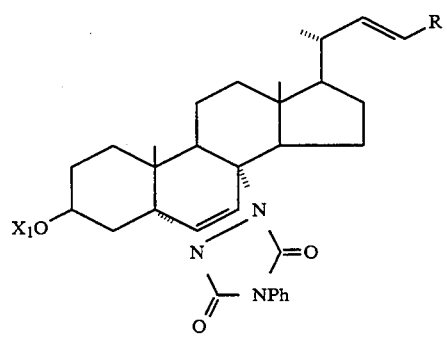

where R and $X_1$ represent the groupings defined above. This steroid intermediate can then be further converted by known reactions to the desired vitamin D compounds.

It is readily apparent that by suitable variation of R in the aryl sulfone derivative used in the above coupling process a range of different vitamin D compounds can be produced.

25-Hydroxylated Compounds ($X_2$ Is Hydroxy)

The reaction sequence illustrated by Process Scheme I presents a specific embodiment of the overall process, whereas Process Scheme II illustrates preparation of an appropriate side chain unit for addition to the steroid-22-aldehyde as shown in Scheme I.

Starting materials for the present process are steroidal 22-aldehydes, such as, for example, the PTAD-diene-protected-22-aldehyde (4) shown in Scheme I (where PTAD refers to the phenyltriazoline-3,5-dione-protecting group shown), which in turn can be prepared from ergosterol by the known steps (Scheme I).

The first step of this process comprises the addition of a suitable side chain fragment. Thus, condensation of aldehyde (4) with a sulfonyl-side chain fragment as shown in Scheme I (sulfone (21), further described below) present in the form of its anion, in an ether or hydrocarbon solvent, provides the hydroxy-sulfone intermediate (5). The anion of the sulfone (21) side chain fragment is generated by treatment of the sulfone with a strong base, such as lithium diethylamide, n-butyl lithium or methyl or ethyl magnesium bromide (or similar Grignard reagent) in an ether or hydrocarbon solvent, and to this solution of sulfone anion the steroid aldehyde (compound 4) as an ether or hydrocarbon solution is then added. The reaction is best effected under an inert atmosphere.

The next step comprises the removal of the hydroxy- and phenylsulfonyl groups in the side chain with formation of the 22(23)-trans-double bond. Thus, treatment of compound (5), in methanol solution saturated with $NaHPO_4$, with sodium amalgam under an inert atmosphere, gives compound (6) featuring the desired trans-22-double bond in the side chain. If desired, the 22-hydroxy group in compound (5) can also be acylated or sulfonylated (e.g. mesylated) prior to the Na/Hg-reduction step, but this is not generally required.

It is to be noted that, as shown in Process Scheme I, addition of the side chain fragment, sulfone (21), to the aldehyde (4), does not cause epimerization at the asymmetric center of carbon 20, i.e. the stereochemistry at that center is retained, as is required. If desired, retention of stereochemistry at carbon 20 may be checked at this stage of the synthesis by the conversion of intermediates of type (6) back to the original aldehyde starting materials. For example, subjecting compound (6) to ozonolysis with reductive work-up, using fully conventional and standard conditions, yields the corresponding C-22-aldehyde, i.e. the aldehyde of structure (4). Spectroscopic and chromatographic comparison of the aldehyde obtained from ozonolysis with the original starting material confirms retention of C-20 stereochemistry.

The next operation of the process involves conversion of these ring B-protected steroids to the desired 5,7-diene intermediate (7). In the case of the PTAD-diene-protected compound (6), this conversion is accomplished in a single step, namely treatment of (6) with a strong hydride reducing agent (e.g. $LiAlH_4$) in an ether solvent at reflux temperature gives the diene (7). The diene (7) is then converted to its 25-hydroxylated form (8) by known procedures in accordance with Scheme I.

Conversion of 5,7-diene (8) to the final vitamin D products (10) or (15) comprises a sequence of several steps. The sequence shown in Process Scheme I involves first the irradiation of an ether or hydrocarbon solution of the 5,7-diene (8) with ultraviolet light to yield the previtamin analog (9) which by warming (50°–90° C.) in a suitable solvent (e.g. ethanol, hexane) undergoes isomerization to the 25-hydroxyvitamin $D_2$ compound (10).

Thereafter, compound (10) may be converted to the 1,25-dihydroxyvitamin $D_2$ compound (15) by the known steps shown in Scheme I. Reference is made to U.S. Pat. Nos. 4,260,549 and 4,554,106 for the prior art relevant to these transformations.

The side chain fragment, sulfone (21), as used in Scheme I is specifically the (R) enantiomer. Therefore, compounds (10) or (15) are obtained as the C-24-R-epimers, 25-hydroxy-24-epi-vitamin $D_2$ (10) or $1\alpha$,25-dihydroxy-24-epi-vitamin $D_2$ (15), respectively. Thus, compound (10) or (15) are prepared in epimerically pure form, and C-24-epimer separation as required in the process disclosed in U.S. Pat. No. 4,448,721, is not necessary. Use of the (S)-epimer of sulfone (21) in the present process yields specifically 25-OH-$D_2$, as well as, of course, the respective 1,25-dihydroxyvitamin $D_2$ compound.

The 5,7-diene (7) may be used as the free hydroxy compound or as its hydroxy-protected form, where the hydroxy-protecting groups (at C-3 and/or C-25) may be acyl, alkylsilyl or alkoxyalkyl groups as previously defined. Thus, the 25-OH-$D_2$ product will be obtained as the free hydroxy compound or, if desired, as the C-3, or C-25-hydroxy-protected, or 3,25-dihydroxy-protected derivatives. Synthesis according to Scheme I would provide the 25-OH-$D_2$ products as the free hydroxy compounds but analogous conversion of 5,7-diene intermediate (7) as the 3-, or 25-protected, or 3,25-di-protected derivative will yield the corresponding hydroxy-protected derivatives of the 25-OH-$D_2$ products.

The individual 25-OH-$D_2$ epimers, i.e. 25-OH-$D_2$ or 25-OH-24-epi-$D_2$ (10) when obtained in the free hydroxy forms, are also conveniently hydroxy-protected at the C-3 or C-25, or at both positions, by conventional reactions known in the art. Thus, 25-OH-$D_2$ may be acylated to yield, for example, the 25-OH-$D_2$-3-acetate, or the corresponding 3,25-diacetate. The 3-monoacetate, in a like fashion, may be further acylated at C-25 by treatment with a different acylating reagent, or, alternatively, the 3,25-diacetate may be selectively hydrolyzed by a mild base (KOH/MeOH) to give the 25-monoacetate, which if desired can be reacylated with a different acyl group at C-3. Other hydroxy-protecting groups can be introduced by analogous known reactions.

In addition to the hydroxy-protected derivatives, the 5,6-trans-isomers of 25-OH-24-epi-$D_2$ is well as the 1,25-dihydroxy compounds are compounds of potential utility in medical applications because of their considerable vitamin D-like activity. These 5,6-trans-compounds are prepared from the 5,6-cis-isomers (i.e. 10 or 15) by iodine catalyzed isomerization according to the procedures of Verloop et al. Rec. Trav. Chim. Pays Bas 78, 1004 (1969), and the corresponding 3- and/or 25-hydroxy-protected derivatives are likewise obtained by analogous isomerization of the corresponding 5,6-cis-acylates, or by hydroxy-protection of the 5,6-trans-25-OH-$D_2$ compounds.

The required side chain fragment, sulfone (21), is itself prepared according to the process shown in Process Scheme II. This synthesis is straight-forward and involves as a first step the reaction of ester (16) in anhydrous tetrahydrofuran (THF) with methyl magnesium bromide to give the diol (17). Diol (17) is dissolved in anhydrous pyridine and reacted with p-toluenesulfonyl chloride to provide the tosylate (18). Tosylate (18) is dissolved in a solution of anhydrous dimethyl formamide and reacted with thiophenol and t-BuOK to yield the sulfide (19). The sulfide (19) in turn is dissolved in dichloromethane and reacted with 3-chloroperoxybenzoic acid to give the hydroxy sulfone compound (20). Pyridinium p-toluenesulfonate is then added to a solution of compound (20) in anhydrous dichloromethane and reacted with dihydropyran to yield the hydroxy protected tetrahydropyranyl sulfone (21a). The corresponding (S)-epimer of sulfone (21) is prepared by the same process, using as starting material the ester corresponding to (16) but having the (S) configuration at carbon-2.

Non-25-Hydroxylated Compounds ($X_2$ Is Hydrogen)

The reaction sequence illustrated by Process Scheme III presents another specific embodiment of the overall process, whereas Process Scheme IV illustrates preparation of an appropriate side chain unit for addition to the steroid-22-aldehyde as shown in Scheme III.

Starting materials for the present process are steroidal 22-aldehydes, such as, for example, the PTAD-diene-protected-22-aldehyde (4) shown in Scheme I (where PTAD refers to the phenyltriazoline-3,5-dione-protecting group shown), which in turn can be prepared from ergosterol by the known steps (Scheme I).

The first step of this process comprises the addition of a suitable side chain fragment. Thus, condensation of aldehyde (4) with a sulfonyl-side chain fragment as shown in the Scheme III (sulfone (35), further described below) present in the form of its anion, in an ether or hydrocarbon solvent, provides the hydroxy-sulfone intermediate (22). The anion of the sulfone (35) side chain fragment is generated by treatment of the sulfone with a strong base, such as lithium diethylamide, n-butyl lithium or methyl or ethyl magnesium bromide (or similar Grignard reagent) in an ether or hydrocarbon solvent, and to this solution of sulfone anion the steroid aldehyde (compound 4) as an ether or hydrocarbon solution is then added. The reaction is best effected under an inert atmosphere.

The next step comprises the removal of the hydroxy- and phenylsulfonyl groups in the side chain with formation of the 22 (23)-trans-double bond. Thus, treatment of compound (22), in methanol solution saturated with $NaHPO_4$, with sodium amalgam under an inert atmosphere, gives compound (23) featuring the desired trans-22-double bond in the side chain. If desired, the 22-hydroxy group in compound (22) can also be acylated or sulfonylated (e.g. mesylated) prior to the Na/Hg-reduction step, but this is not generally required.

It is to be noted that, as shown in Process Scheme III, addition of the side chain fragment, sulfone (35), to the aldehyde (4), does not cause epimerization at the asymmetric center of carbon 20, i.e. the stereochemistry at that center is retained, as is required. If desired, retention of stereochemistry at carbon 20 may be checked at this stage of the synthesis by the conversion of intermediates of type (23) back to the original aldehyde starting materials. For example, subjecting compound (23) to ozonolysis with reductive work-up, using fully conventional and standard conditions, yields the corresponding C-22-aldehyde, i.e. the aldehyde of structure (4). Spectroscopic and chromatographic comparison of the aldehyde obtained from ozonolysis with the original starting material confirms retention of C-20 stereochemistry.

The next operation of the process involves conversion of these ring B-protected steroids to the desired 5,7-diene intermediate (24). In the case of the PTAD-diene-protected compound (23), this conversion is accomplished in a single step, namely treatment of (23) with a strong hydride reducing agent (e.g. $LiAlH_4$) in an ether solvent at reflux temperature gives the diene (24).

Conversion of 5,7-diene (24) to the final vitamin D products (26) or (31) comprises a sequence of several steps. The sequence shown in Process Scheme III involves first the irradiation of an ether or hydrocarbon solution of the 5,7-diene (24) with ultraviolet light to yield the previtamin analog (25) which by warming (50°–90° C.) in a suitable solvent (e.g. ethanol, hexane) undergoes isomerization to the vitamin $D_2$ compound (26).

Thereafter, compound (26) may be converted to the 1α-hydroxyvitamin $D_2$ compound (31) by the known steps shown in Scheme III. Reference is made to U.S. Pat. Nos. 4,260,549 and 4,554,106 for the prior art relevant to these transformations.

The side chain fragment, sulfone (35), as used in Scheme III is specifically the (R) enantiomer. Therefore, compounds (26) or (31) are obtained as the C-24-R-epimers, 24-epi-vitamin $D_2$ (26) or 1α-hydroxy-24-epi-vitamin $D_2$ (31), respectively. Thus, compounds (26) or (31) are prepared in epimerically pure form, and C-24-epimer separation as required in the process disclosed in U.S. Pat. No. No 4,448,721 is not necessary. Use of the (S)-epimer of sulfone (35) in the present process yields specifically vitamin $D_2$, as well as, of course, the respective 1α-hydroxyvitamin $D_2$ compound.

The 5,7-diene (24) may be used as the free hydroxy compound or as its hydroxy-protected form, where the hydroxy-protecting groups (at C-3) may be acyl, alkyl-silyl or alkoxyalkyl groups as previously defined. Thus, the vitamin $D_2$ product will be obtained as the free hydroxy compound or, if desired, as the C-3-hydroxy-protected derivatives. Synthesis according to Scheme III would provide the vitamin $D_2$ products as the free hydroxy compounds but analogous conversion of 5,7-diene intermediate (24) as the 3-protected, derivative will yield the corresponding hydroxy-protected derivatives of the vitamin $D_2$ products.

The individual vitamin $D_2$ epimers, i.e. vitamin $D_2$ or 24-epi-$D_2$ (26) when obtained in the free hydroxy forms, are also conveniently hydroxy-protected at the C-3 position, by conventional reactions known in the art. Thus, vitamin $D_2$ may be acylated to yield, for example, the vitamin $D_2$-3-acetate. Other hydroxy-protecting groups can be introduced by analogous known reactions.

In addition to the hydroxy-protected derivatives, the 5,6-trans-isomers of 24-epi-$D_2$ as well as the 1α-hydroxy compounds are compounds of potential utility in medical applications because of their considerable vitamin D-like activity. These 5,6-trans-compounds are prepared from the 5,6-cis-isomers (i.e. 26 or 31) by iodine catalyzed isomerization according to the procedures of Verloop et al. Rec. Tray. Chim. Pays Bas 78, 1004 (1969), and the corresponding 3-hydroxy-protected derivatives are likewise obtained by analogous isomerization of the corresponding 5,6-cis-acylates, or by hydroxy-protection of the 5,6-trans-$D_2$ compounds.

The required side chain fragment, sulfone (35), can be prepared according to Perlman et al, supra, or according to the process shown in Process Scheme IV. This synthesis is straightforward and involves as a first step dissolving alcohol (32) in anhydrous pyridine and reacting it with p-toluenesulfonyl chloride to provide the tosylate (33). Tosylate (33) is dissolved in a solution of anhydrous dimethyl formamide and reacted with thiophenol and t-BuOK to yield the sulfide (34). The sulfide (34) in turn is dissolved in dichloromethane and reacted with 3-chloroperoxybenzoic acid to give the sulfone compound (35). The corresponding (S)-epimer of sulfone (35) can also be prepared according to Perlman et al or according to Process Scheme IV, using as starting material the alcohol corresponding to (32) but having the (S) configuration at carbon-2.

Analog Compounds

Furthermore, the present process also serves as a convenient method for the synthesis of side chain homologated vitamin $D_2$ analogs where the carbon at any one of the side chain positions designated as 24, 26 and 27 may be homologated, of the formula (40) shown below, or of the corresponding 25-hydroxy-analogs and/or 1α-hydroxy-analogs,

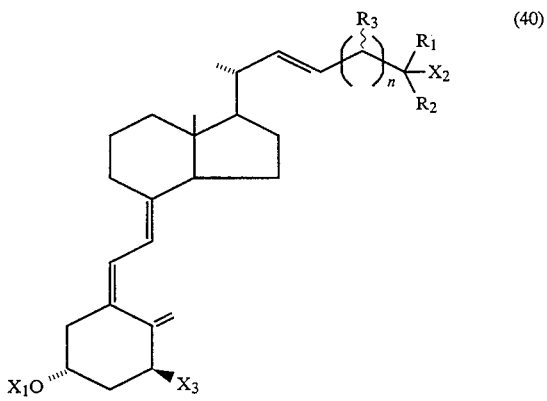
(40)

where n is an integer having a value of from 1 to 5, $X_1$ is selected from hydrogen and a hydroxy-protecting group, $X_2$ is selected from hydrogen, hydroxy anti protected hydroxy, $X_3$ is selected from hydrogen, hydroxy, and protected hydroxy, $R_3$ is alkyl, hydroxy, protected hydroxy, hydrogen or fluorine, and where $R_1$ and $R_2$, which may be the same or different, is an alkyl group or an aryl group and where the configuration about carbon 24 has either the (R)- or the (S)-stereochemical orientation. These compounds are prepared by condensing compound (4) with the appropriate alkyl or aryl side chain fragment as shown by the following formulae,

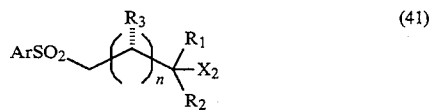
(41)

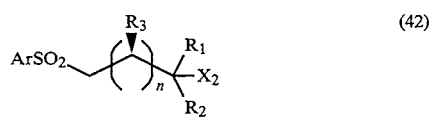
(42)

where $X_2$, $R_1$, $R_2$, $R_3$ and n are as defined above.

The use of compounds where (41) and (42) as side chain units in the synthetic process depicted as in Schemes I and III, then provides the 25-OH-$D_2$- or 25-OH-24-epi-$D_2$-homologs of general structure (40) where $R_1$, $R_2$ and $R_3$ represent alkyl or aryl residues or other substitutes as defined above. The products of general structure (40) can then be 1α-hydroxylated according to known methods (See U.S. Pat. Nos. 4,260,549 and 4,554,106) so as to obtain the corresponding 1α-hydroxylated vitamin D homologs.

Since the compounds where $R_1$, $R_2$ or $R_3$ represent higher homologs of methyl, are generally more lipophilic, the alkyl- or aryl-analogues represented by structure (40) above or their 5,6-trans-isomers, are expected to have utility in applications where a greater degree of lipophilicity is desired.

The present invention is further described by means of the following illustration. In this illustration, numerals designating specific products, e.g. compounds 1, 2, 3 etc. refer to the structures so numbered in Process Schemes I or II.

EXAMPLE 1

Ergosterol Method

To a solution of 50 g (0.13 mol) of ergosterol in 300 ml of anhydrous pyridine was added 33.3 ml (0.35 mol) of acetic anhydride. The mixture was stirred at room temperature overnight and 600 ml of water was added. The precipitate was filtered off, washed several times with 200 ml of water and recrystallized from ethanol to obtain 2, 42.0 g (76%). [yellowish crystal]

To a solution of 33 g (0.075 mmol) of 2 in 500 ml of chloroform was added 13.2 g (0.075 mmol) of 4-phenyl-1,2,4-triazoline-3,5-dione. The solution was stirred at room temperature for 30 min and 5 ml of pyridine was added. The solution was cooled at −78° C. and treated with an ozone-oxygen mixture for 30 min (TLC control) and thoroughly purged with nitrogen. 50 ml of dimethyl sulfide was added and the mixture was washed with 300 ml of water, 200 ml of 2N HCl (twice) and 300 ml of water. The organic layer was separated and each washing was extracted with 400 ml and 200 ml of chloroform. The combined extract was dried over $Na_2SO_4$ and concentrated in vacuo. The residue was purfied on a silica gel column (5.06×63 cm, 550 g of 150~425 μm silica gel) using a mixture of ethyl acetate and hexane as eluant. 20.5 g (50%) of 4 was eluted with 30% ethyl acetate in hexane. To increase yield, the recovered 3 (eluted with 15% ethyl acetate in hexane) was treated with an ozone-oxygen mixture as above.

To a stirred solution of 12.1 g (37.1 mmol) of sulfone 21, 5.10 ml (36.4 mmol) of diisopropyl amine and 100 ml of anhydrous tetrahydrofuran (containing 1,10-phenanthroline as indicator) under nitrogen atmosphere at −78° C. was added 22.7 ml (36.3 mml) of n-BuLi (1.6M in hexane). The solution was stirred under nitrogen at −78° C. for 30 min, then 10.0 g (18.3 mmol) of 4 in 40 ml of anhydrous tetrahydrofuran was added. The mixture was stirred at −78° C. for 1 hr, decomposed by the addition of 100 ml of saturated $NH_4Cl$ solution, warmed to 0° C. and extracted three times with 100 ml of ethyl acetate. Each extract was washed with 100 ml of saturated NaCl solution, dried over $Na_2SO_4$ and concentrated in vacuo. The residue was purified on a silica gel column (3.2×60 cm, 150 g of 75~150 μm silica gel). The unreacted sulfone 21 was eluted with benzene and 14.7 g (92%) of 5 was eluted with ethyl acetate.

A mixture of 14.7 g (16.9 mmol) of hydroxysulfone 5, 110 g of 5% sodium amalgam and 400 ml of methanol saturated with $Na_2HPO_4$ was stirred under nitrogen atmosphere at 5° C. for 20 hrs. The reaction solution was decanted and concentrated in vacuo. The residue was dissolved in 200 ml of ethyl acetate and washed with 400 ml and 200 ml of water. The ethyl acetate extract was separated and each of washing was extracted twice with 200 ml of ethyl acetate. The combined extract was dried over $Na_2SO_4$ and concentrated in vacuo. 10.5 g (91%) of 6 was obtained.

To a solution of 10.5 g (15.4 mmol) of 6 in 400 ml of tetrahydrofuran was added 11.5 g (303.0 mmol) of $LiAlH_4$. The mixture was heated under reflux and nitrogen atmosphere for 3 hrs, cooled with ice water and decomposed by the dropwise addition of 40 ml of ethyl acetate and 60 ml of water. Then, the mixture was filtered and the filtrate was concentrated in vacuo. The residue was dissolved in 200 ml of ethyl acetate and washed twice with 200 ml of saturated NaCl solution. The ethyl acetate extract was separated and each washing was extracted with 200 ml of ethyl acetate. The combined extract was dried over $Na_2SO_4$ and concentrated in vacuo. Then, the residue was purified on a silica gel column (3.2×25 cm, 80 g of 75 150 μm silica gel) and 4.8 g (63%) of 7 was eluted with 5% ether in benzene as eluant [yellow foam].

To a solution of 4.4 g (8.9 mmol) of 7 in 200 ml of methanol and 130 ml of dichloromethane was added 2.0 g (7.9 mmol) of pyridinium p-toluenesulfonate. The mixture was stirred at room temperature overnight, dissolved in 300 ml of saturated NaCl solution and extracted three times with 400 ml of dichloromethane. Each extract was washed with 400 ml of saturated NaCl solution, combined, dried over $Na_2SO_4$ and concentrated in vacuo. The residue was recrystallized from ethanol to obtain 2.5 g (68%) of 8 [white crystal]. To increase yield, the mother liquor was concentrated in vacuo, purified with chromatography and recrystallized from ethanol.

1.50 g (3.6 mmol) of 8 was dispersed in 500 ml of a mixture of ether and benzene (4:1) and irradiated with stirring under nitrogen in a water-cooled quartz immersion well equipped with an ozone free filter using Eikosha's high-pressure UV lamp for 25 min. The reaction was monitored by HPLC using Lichrosorb Si 60 (5 μm) column and 3% 2-propanol in hexane at 265 nm.

The solution was concentrated in vacuo, redissolved in 100 ml of ethanol and heated under reflux and nitrogen for 3 hrs. Then, the solution was concentrated in vacuo and the residue was purified on a silica gel column (3.2×50 cm, 170 g of 75~150 μm of silica gel) using a mixture of ethyl acetate in hexane. 074 g (50%) of 10 was eluted with 20% ethyl acetate in hexane. [white foam]

To a solution of 1.50 g (3.6 mmol) of 10 in 15 ml of anhydrous pyridine was added 1.50 g (7.9 mmol) of tosyl chloride. The mixture was stirred under nitrogen at 5° C. for 20 hrs. Then, the solution was poured into 200 ml of cold saturated $NaHCO_3$ solution. The mixture was allowed to stand for 30 min and extracted three times with 150 ml of a mixture of ether and dichloromethane (4:1). Each extract was washed with 150 ml of saturated NaCl solution, 150 ml of cold diluted HCl solution for twice, 150 ml of saturated NaCl solution, 150 ml of saturated $NaHCO_3$ solution and 150 ml of saturated NaCl solution. The combined extract was dried over $Na_2SO_4$ and concentrated in vacuo. 1.90 g (92%) of 11 was obtained and converted to 12 without further purification. [white foam]

4.40 g of anhydrous $KHCO_3$ was dissolved in 200 ml of anhydrous methanol under nitrogen at 50° C. To this solution was added dropwise a solution of 1.90 g (3.4 mmol) of 11 in 30 ml of anhydrous dichloromethane. The mixture was stirred under nitrogen at 50° C. for 21 hrs. Then, the solution was concentrated in vacuo, the residue was dissolved in 200 ml of a mixture of ether and dichloromethane (4:1) and washed twice with 100 ml of water. The organic extract was separated and each washing was extracted twice with 100 ml of the same mixture of ether and dichloromethane. The combined extract was dried over $Na_2SO_4$ and concentrated in vacuo to obtain 1.50 g (105%) of 12 which was hydroxylated without further purification. [yellow oil]

2.7 ml (8.1 mmol) of tert-butyl hydroperoxide (3.0M in 2,2-4-trimethylpentane) was added to a suspension of 220 mg (2.0 mmol) of selenium dioxide in 75 ml of anhydrous dichloromethane. The mixture was stirred at room temperature under nitrogen for 30 min. 0.3 ml of anhydrous pyridine was added followed by a solution of 1.50 g (3.5 mmol) of 12 in 30 ml of anhydrous dichloromethane. The mixture was stirred under nitrogen at room temperature for 30 min and heated under reflux for 10 min. Then, 50 ml of 10% NaOH solution was added and the mixture was extracted with 200, 100 and 100 ml of ether. Each extract was washed with 50 ml of 10% NaOH solution and 50 ml of saturated NaCl solution. The combined extract was dried over $Na_2SO_4$ and concentrated in vacuo. The residue was purified on a silica gel column (3.2 cm×15 cm, 50 g of 75~150 μm silica gel) using a mixture of ethyl acetate in hexane as eluant. 581 mg (37%) of 13 was eluted with 30% ethyl acetate in hexane. [yellow oil]

581 mg (1.3 mmol) of 13 was dissolved in 5 ml of acetic acid and heated at 50° C. under nitrogen for 1 hr. Then, the solution was poured over ice and neutralized with 100 ml of saturated $NaHCO_3$ solution. The mixture was extracted three times with 150 ml of a mixture of ether and dichlormethane (4:1) Each extract was washed with 100 ml of saturated $NaHCO_3$ solution and 100 ml of saturated NaCl solution. The combined extract was dried over $Na_2SO_4$ and concentrated in vacuo. Then, to a solution of the residue in 10 ml of ethyl acetate was added 120 mg of maleic anhydride and the mixture was allowed to stand under nitrogen at room temperature for 2 hrs. Then, the solution was concentrated in vacuo, the residue was redissolved in 50 ml of ether. 50 ml of 0.1N KOH in methanol was added, the solution was stirred at room temperature for 1.5 hrs. and concentrated in vacuo. The residue was dissolved in 100 ml of a mixture of ether and dichloromethane (4:1) and washed with 50 ml of 10% NaOH solution for twice and 50 ml of saturated NaCl solution. The organic extract was separated and each of washing was extracted twice with 100 ml of the same mixture of ether and dichloromethane. The combined extract was dried over $Na_2SO_4$ and concentrated in vacuo. The residue was purified on a silica gel column (2.3×8.0 cm, 10 g of 45~75 μm silica gel) using a mixture of ethyl acetate in hexane as eluant. 310 mg of 15 was eluted with 30% ethyl acetate in hexane, combined with another 337 mg of 15 and recrystallized from methyl formate.

EXAMPLE 2

Intermediates for Side Chain 20 g (0.169 mol) of methyl (R)-(−)-3-hydroxy-2-methyl propionate 16 was dissolved in 60 ml of anhydrous tetrahydrofuran and added under nitrogen atmosphere and ice cooling to a stirred solution of 245 ml (0.735 mol) of methylmagnesium bromide (3.0M solution in ether). At the end of the addition 100 ml of anhydrous tetrahydrofuran was added to facilitate stirring. The mixture was stirred at room temperature for 2 hrs, decomposed by the careful addition of 150 ml of 5N HCl with ice cooling and extracted three times with 200 ml of ether. Each extract was washed with 150 ml of saturated NaCl solution, combined and dried over $Na_2SO_4$. Evaporation afforded 16.4 g (82%) of 17 as yellow oil.

A mixture of 16.4 g (0.139 mol) of 17, 26.5 g (0.139 mol) of tosyl chloride and 30 ml of pyridine was stirred at 4° C. overnight. Then, the reaction mixture was dissolved in 300 ml of ether and washed with 200 ml of water, 200 ml of diluted HCl, 200 ml of water and 200 ml of saturated $NaHCO_3$ solution. The ether extract was separated and each washing was extracted twice with 200 ml of ether. The combined extract was dried over $Na_2SO_4$ and concentrated in vacuo. The residue was purified on a silica gel column (5.5×20 cm, 200 g of 150 425 m silica gel) and 32.1 g (85%) of tosylate (18) was eluted with 10~20% ethyl acetate in hexane. [red oil]

To a stirred solution of 14.4 g (0.131 mol) of thiophenol in 70 ml of anhydrous dimethyl formamide 14.4 g (0.131 mol) of t-BuOK was added followed by 32.1 g (0.118 mol) of 10 in 90 ml anhydrous dimethyl formamide. The mixture was stirred overnight, dissolved in 300 ml of ice water and extracted with 300,200 and 200 ml of ethyl acetate. Each extract was washed with 200 ml saturated $NaHCO_3$ solution and water, combined, dried over $Na_2SO_4$ and concentrated in vacuo 28.0 g (113% containing dimethyl formamide) of 19 was obtained and was oxidized without further purification. [red oil]

28.0 (0.118 mol) of 19 was dissolved in 400 ml of dichloromethane and cooled with ice water. To this solution was added 51.7 g (0.300 mol) of m-chloroperbenzoic acid slowly, the mixture was stirred at room temperature for 2 hrs. and filtered. The filtrate was washed with 300 ml of saturated $NaHCO_3$ solution for twice, 300 ml of saturated $Na_2SO_3$ solution for twice and 300 ml of saturated $NaHCO_3$ solution. The organic phase was separated and each washing was extracted twice with 300 ml of dichloromethane. The combined extract was dried over $Na_2SO_4$, concentrated in vacuo and recrystallized from a mixture of ethyl acetate in hexane to obtain 20 25.2 g (88%). [white crystals]

To a stirred solution of 20 g (0.083 mol) of 20 in 50 ml of dichloromethane was added 20 ml (0.221 mol) of freshly distilled 2,3-dihydropyran followed by 0.8 g of pyridinium p-toluenesulfonate. The mixture was stirred at room temperature for 2 hrs. and washed twice with saturated NaCl solution. The organic phase was separated and each of washing was extracted twice with 50 ml of dichloromethane. The combined extract was dried over $Na_2SO_4$ and concentrated in vacuo. The residue was purified on a silica gel column (3.2×45 cm, 150 g of 75~150 μm silica gel) and 26.0 g (96%) of 21a was eluted with benzene as eluant. [colorless oil]

EXAMPLE 3

To a solution of ergosterol 1 in anhydrous pyridine is added acetic anhydride. The mixture is stirred at room temperature overnight and water is added. The precipitate is filtered off, washed several times with water and recrystallized from ethanol to obtain 2.

To a solution of the precipitate 2 in chloroform is added 4-phenyl-1,2,4-triazoline-3,5-dione. The solution is stirred at room temperature and pyridine is added. The solution is cooled and treated with an ozone-oxygen mixture (TLC control) and thoroughly purged with nitrogen. Dimethyl sulfide is added and the mixture is washed with water, 2N HCl and then water again. The organic layer is separated and each washing is extracted with chloroform. The combined extract is dried over $Na_2SO_4$ and concentrated in vacuo. The residue is purified by silica gel chromatography to obtain compound 4.

To a stirred solution of sulfone 35, diisopropyl amine and anhydrous tetrahydrofuran (containing 1,10-phenanthroline as indicator) under nitrogen atmosphere is added n-BuLi (1.6M in hexane). The solution is stirred under nitrogen, then, compound 4 in anhydrous tetrahydrofuran is added. The mixture is stirred, decomposed by the addition of saturated $NH_4Cl$ solution, warmed and extracted three times with ethyl acetate. Each extract is washed with saturated NaCl solution, dried over $Na_2SO_4$ and concentrated in vacuo. The residue is purified on a silica gel column to afford compound 22.

A mixture of hydroxysulfones 22, 5% sodium amalgum and methanol saturated with $Na_2HPO_4$ is stirred under nitrogen atmosphere. The reaction solution is decanted and concentrated in vacuo. The residue is dissolved in ethyl acetate and washed with water. The ethyl acetate extract is separated and each washing is extracted twice with ethyl acetate. The combined extract is dried over $Na_2SO_4$ and concentrated in vacuo to obtain 23.

To a solution of compound 23 in tetrahydrofuran is added $LiAlH_4$. The mixture is heated under reflux and nitrogen atmosphere, cooled with ice water and decomposed by the dropwise addition of ethyl acetate and water. Then, the mixture is filtered and the lilt rate is concentrated in vacuo. The residue is dissolved in ethyl acetate and washed twice with saturated NaCl solution. The ethyl acetate extract is separated and each washing is extracted with ethyl acetate. The combined extract is dried over $Na_2SO_4$ and concentrated in vacuo. Then, the residue is purified on a silica gel column to provide compound 24.

Compound 24 is dispersed in a mixture of ether and benzene (4:1) and irradiated with stirring under nitrogen in a water-cooled quartz immersion well equipped with an ozone free filter using a high-pressure UV lamp. The reaction may be monitored by HPLC.

The solution is concentrated in vacuo, redissolved in ethanol and heated under reflux and nitrogen. Then, the solution is concentrated in vacuo and the residue is purified on a silica gel column to obtain compound 26.

To a solution of compound 26 in anhydrous pyridine is added tosyl chloride. The mixture is stirred under nitrogen. Then, the solution is poured into a cold saturated $NaHCO_3$ solution. The mixture is allowed to stand for 30min and extracted three times with a mixture of ether and dichloromethane (4:1). Each extract is washed with saturated NaCl solution, cold diluted HCl solution twice, saturated NaCl solution, saturated $NaHCO_3$ solution and saturated NaCl solution. The combined extract is dried over $Na_2SO_4$ and concentrated in vacuo. Compound 27 is obtained and converted to 28 without further purification.

Anhydrous $KHCO_3$ is dissolved in anhydrous methanol under nitrogen. To this solution is added dropwise a solution of compound 27 in anhydrous dichloromethane. The mixture is stirred under nitrogen. Then, the solution is concentrated in vacuo, the residue is dissolved in a mixture of ether and dichloromethane (4:1) and washed twice with water. The organic extract is separated and each washing is extracted twice with the same mixture of ether and dichloromethane. The combined extract is dried over $Na_2SO_4$ and concentrated in vacuo to obtain Compound 28 which is hydroxylated without further purification.

Tert-butyl hydroperoxide (3.0M in 2,2-4-trimethyl-pentane) is added to a suspension of selenium dioxide in anhydrous dichloromethane. The mixture is stirred at room temperature under nitrogen. Anhydrous pyridine is added followed by a solution of compound 28 in anhydrous dichloromethane. The mixture is stirred under nitrogen at room temperature and heated under reflux. Then, a 10% NaOH solution is added and the mixture is extracted with ether. Each extract is washed with a 10% NaOH solution and a saturated NaCl solution. The combined extract is dried over $Na_2SO_4$ and concentrated in vacuo. The residue is purified on a silica gel column to obtain compound 29.

Compound 29 is dissolved in acetic acid and heated under nitrogen. Then, the solution is poured over ice and neutralized with saturated $NaHCO_3$ solution. The mixture is extracted three times with a mixture of ether and dichloromethane (4:1). Each extract is washed with a saturated $NaHCO_3$ solution and a saturated NaCl solution. The combined extract is dried over $Na_2SO_4$ and concentrated in vacuo. Then, to a solution of the residue in ethyl acetate is added maleic anhydride and the mixture is allowed to stand under nitrogen at room temperature. Then, the solution is concentrated in vacuo, the residue is redissolved in ether. KOH in methanol is added, the solution is stirred at room temperature and concentrated in vacuo. The residue is dissolved in a mixture of ether and dichloromethane (4:1) and washed with 10% NaOH solution twice and a saturated NaCl solution. The organic extract is separated and each washing is extracted twice with the same mixture of ether and dichloromethane. The combined extract is dried over $Na_2SO_4$ and concentrated in vacuo. The residue is purified on a silica gel column using a mixture of ethyl acetate in hexane as eluant to obtain compound 31.

EXAMPLE 4

Intermediates for Side Chain

A mixture of compound 32, tosyl chloride and pyridine is stirred overnight. Then, the reaction mixture is dissolved in ether and washed with water, diluted HCl, water and saturated $NaHCO_3$ solution. The ether extract is separated and each washing is extracted twice with ether. The combined extract is dried over $Na_2SO_4$ and concentrated in vacuo. The residue is purified on a silica gel column to give tosylate (33).

To a stirred solution of thiophenol in anhydrous dimethyl formamide t-BuOK is added followed by compound 33 in anhydrous dimethyl formamide. The mixture is stirred overnight, dissolved in ice water and extracted with ethyl acetate. Each extract is washed with a saturated $NaHCO_3$ solution and water, combined, dried over $Na_2SO_4$ and concentrated in vacuo. Compound 34 is obtained and oxidized without further purification.

Compound 34 is dissolved in dichloromethane and cooled with ice water. To this solution is added m-chloroperbenzoic acid slowly, the mixture is stirred at room temperature for 2 hrs. and filtered. The filtrate is washed with a saturated $NaHCO_3$ solution twice, a saturated $Na_2SO_3$ solution twice and a saturated $NaHCO_3$ solution. The organic phase is separated and each washing is extracted twice with dichloromethane. The combined extract is dried over $Na_2SO_4$, concentrated in vacuo and recrystallized from a mixture of ethyl acetate in hexane to form compound 35.

EXAMPLE 5

Alternative Synthesis

As an alternative to the above-described synthesis, the compounds of the present invention may be prepared in accordance with the procedures set forth in U.S. Pat. No. 4,847,012. The following illustrates the preparation of 24-epi-26,27-dihomo 1α,25-dihydroxyvitamin $D_2$. This compound is distinguished from the previously known 24-epi-1α,25-dihydroxyvitamin $D_2$ by homologation at the 26,27 positions. As is readily apparent to those skilled in this art, the following described synthesis may be readily adapted to making the other homologated compounds disclosed herein by selecting the appropriate side chain unit and/or vitamin D nucleus for the condensation step.

The synthesis of 24-epi-26,27-dihomo-1α,25-dihydroxyvitamin $D_2$ requires the construction of an appropriate side chain unit having the desired (S) stereochemistry an the carbon center that is to become carbon-(24 R) in the target compound, and the condensation of the side chain unit with a suitable 1α-hydroxylated vitamin D nucleus so as to generate the desired final product.

Referring first to Scheme 5, the synthesis of the optically active side chain unit comprised the conversion of the commercially available (R)-(−)-3-hydroxy-2-methylpropionate 41 with ethylmagnesium bromide to the diol 42. This was converted to tosylate 43, then treated with potassium thiophenoxide in alkaline DMF to give sulfide 44. This in turn was oxidized with 3-chloroperbenzoic acid to afford sulfone 45. The very hindered hydroxy of sulfone could not be protected by standard methodology. However, it was successfully protected by the use of triethylsilyltriflate in triethylamine to give the protected sulfone 46.

For the preparation of the desired 24-epi-26,27-dihomo-1α,25-dihydroxyvitamin $D_2$, one is referred to Scheme 6. In Scheme 6, (4S)-3-ethyl-2-methyl-5-phenylsulfonyl-3-triethylsilyloxypentane 46, as obtained by the above procedure, was reacted with the known 1α-hydroxyvitamin D-22 aldehyde derivative 47, using the general procedures of Kutner et al., J. Org. Chem., 53, 3450 (1988). This condensation yields the side chain adduct represented by structure 48, which is then reduced with a metal amalgam to provide the hydroxy protected (24R)-26 27-dihomo-1α,25-dihydroxyvitamin $D_2$ 49. Upon removal of the hydroxy protecting groups according to standard procedures the desired 24-epi-26,27-dihomo-1α,25-dihydroxyvitamin $D_2$ 50 is obtained.

(4S)-3-Ethyl-4-methyl-5-phenylsulfonyl-3-(triethylsilyloxy)-pentane (46)

A solution of 3.3 g (28 mmol) methyl (R)-(−)-3-hydroxy-2-methylpropionate 41 in 5 mL of anhydrous THF was cooled to 0° C. and added dropwise with vigorous stirring, over 15 min, under argon, to a solution of ethylmagnesium bromide (55 mL of 2M in THF) at −10° C. The reaction mixture was stirred 2 h at room temperature, then quenched with 15 mL of 1:1 diluted HCl. The water phase was extracted with ether, dried over anh. $MgSO_4$, filtered and evaporated to give 3.0 g (74%) of the crude diol 42.

The crude diol 42 (3 g) (20.5 mmol) was dissolved in 8 mL of anhydrous pyridine and 4.7 g (24.7 mmol) of p-toluenesulfonyl chloride was added with stirring at 0° C. The mixture was kept for 16 h at 4° C. and quenched with ice water. The water phase was extracted with ether and the ether phase was washed with ice cold 1N. HCl, saturated $CuSO_4$ solution, water, $NaHCO_3$ solution, brine and dried over anh. $MgSO_4$, filtered and evaporated. The crude oil was purified by silica gel column chromatography with ethyl acetate-hexane mixtures to give 4.4 g (73%) tosylate 43 as a colorless oil.

To a stirred solution of 1.62 g (14.7 mmol) of thiophenol and 1.65 g (14.7 mmol) of potassium tert-butoxide in 5 mL of anhydrous dimethylformamide was added 3.94 g (13.1 mmole) of the tosylate 43 in 2 mL of anhydrous dimethyl formamide. The react ion mixture was stirred at room temperature overnight, poured on water and extracted with ether. The organic layer was washed with aqueous sodium carbonate and water and dried ($MgSO_4$). Solvents were removed in vacuo and the crude oil was purified by silica gel chromatography with hexane-ethyl acetate to give sulfide 44 (2.5 g) (85%) as a colorless oil.

Sulfide 44 (2.4 g. 10 mmol) was then dissolved in 36 mL of dry dichloromethane and 3.0 g (17.4 mmol) 3-. chloroperbenzoic acid was added in portions with occasional cooling. The mixture was stirred for 2 h and quenched with 10% sodium bicarbonate. The combined organic extracts were washed with aqueous sodium sulfite, and brine and dried over anh. $MgSO_4$. The solvent was removed in vacuo and the crude oil was purified by silica gel flash chromatography using hexane ethyl acetate to afford sulfone 45 1.98 g (67%) as a colorless liquid. $[\alpha]^{22}D$: +9.2 (c=5.2, $CHCl_3$) Anal. Calcd for $C_{14}H_{22}O_3S$: C, 62.19; H, 8.20; S, 11.86. Found: C, 62.26; H, 8.14; S, 11.85, $^1H$ NMR (500 MHz, $CDCl_3$) δ 1.10 (3H, m, $4-CH_5$) 2.30 (1H, m, 4-CH), 2.84 (1H, m, 5-CH) 3.52 (1H, m, 5-CH), 7.57, 7.66 and 7.92 (5H, m, Ar-H). Mass spectrum m/z (rel. intensity) 271 (M++1) (10), 265 (8), 253 (100), 241.

0.87 g (3.2 mmol) dry sulfone 45 was dissolved in 5 mL of anhydrous dichloromethane, cooled to 0° C. and 5 mL of anhydrous triethylamine added followed by 3 mL (13 mmol) of triethylsilyl triflate under argon and 0° C. The mixture was stirred at room temperature for 1.5 h, ether added and the ether phase washed with ice cold water, brine and dried ($MgSO_4$) and evaporated. The residue was purified by flash chromatography with 10% ethyl acetate in hexane to give 1.45 g (99%) of the triethylsilylated sulfone 46. $^1H$ NMR (500 MHz, $CDCl_3$) δ 1.09 (3H, m, $4-CH_3$), 2.28 (1H, m, 4-CH), 2.85 (1H, m, 5-CH), 3.46 (1H, m, 5-CH). Mass spectrum m/z (relative intensive) 383 (38), 369 (100), 355 (99), 325 (35) 77, 59.

24-Epi-26,27-Dihomo-1α,25-dihydroxyvitamin $D_2$ (50)

To a stirred solution of 24 mg (42 μmol) triethylsilyloxysulfone 46 in 300 μL anhydrous tetrahydrofuran containing 1,10-phenanthroline as an indicator was added under argon at −78° C. 8 μL (60 μmol) diisopropylamine followed by 32 μL (51 μmol) of solution of 1.5M n.BuLi in hexane. The solution was stirred at −78° C. for 30 min (orange-brown color) and 5 mg (7.7 μmol) of protected aldehyde 47 in 300 μL anhydrous tetrahydrofuran was added and the mixture stirred under argon at −78° C. for 1 h. The mixture was quenched with cold saturated $NH_4Cl$ solution, warmed to 0° C. and extracted with ethyl acetate, and the organic phase washed with saturated NaCl solution. The organic phase was dried over anhydrous $MgSO_4$, filtered and evaporated. The residue was purified by preparative HPLC (Zorbax Sil 9.4×25 cm column) using 10% ethylacetate in hexane 108 mg of recovered aldehyde 47 and 6 mg of crude product 48.

A saturated solution of $Na_2HPO_4$ in methanol (1 mL) was added to a stirred solution of 1.2 mg hydroxysulfone 48 in 10 mL of anhydrous tetrahydrofuran, followed by 160 mg of powdered anhydrous $Na_2HPO_4$. The mixture was cooled to 0° C. and fresh 5% sodium amalgam (cca 400 mg) was added. The mixture was stirred at 5° C. for 20 h. A mixture of 1:1 hexane ethyl acetate (5 mL) was then added and the organic layer decanted. The solid material was 3× more extracted with ethyl acetate-hexane. The combined organic phase was washed with saturated NaCl solution and filtered through a SepPak cartridge and evaporated. Final purification by HPLC (Zorbax Sil 9.4×25 cm column) (10% ethyl acetate in hexane) gave 0.650 mg (66%) of the protected vitamin $D_2$ analogue 49.

49 was dissolved in 0.5 mL of anhydrous tetrahydrofuran followed by the addition of 0.5 mL of tetrabutylammonium fluoride in tetrahydrofuran. The mixture was stirred under argon at 55° C. for 1 h, cooled and 5 mL of ether added. The organic phase was washed with 10% solution of $NaHCO_3$, brine and dried over anhydrous $MgSO_4$, filtered and evaporated. The residue was dissolved in 20% 2-propanol in hexane and passed through a silica gel SepPak column. Preparative HPLC (Zorbax Sil 9.4×25 cm column) in 20% 2-propanol in hexane gave 126 μg (35%) 24-epi-26,27-dihomo-1,α25-dihydroxyvitamin $D_2$ 50.

24-epi-26, 27-dihomo-1,25-dihydroxyvitamin $D_2$ exhibited the following spectral properties: UV (EtOH) $\lambda_{max}$ 264 nm, $\lambda_{min}$ 228 nm; MS m/z (relative intensity) 456 (M+, 6), 438 (10), 420 (8), 402 (4), 352 (10), 269 (6), 251 (8), 135 (28), 134 (33), 87 (100), 57 (35); $^1H$ NMR ($CDCl_3$) δ 0.55 (3H, S $18-CH_3$), 0.97 (3H, d, J=6.9 Hz, $28-CH_3$), 1.01 (3H, d, J=6.6 Hz, $21-CH_3$), 4.23 (1H, m, 3H), 4.43 (1H, m, 1-H), 4.99 (1H, br s, 19Z-H), 5.30 (2H, m, 22-H and 23-H), 5.31 (1H, br, s. 19E-H), 6.01 (1H, d, J=11.25 Hz, 7-H), 6.37 (1H, d, J=11.3 Hz, 6H). Exact mass calcd for $C_{30}H_{48}O_3$: 456.3603. Found 456.3603.

Biological Activity of
26,27-Dihomo-1α-Hydroxyvitamin $D_2$;
26,27-Dihomo-1α-Hydroxy-24-epi-Vitamin $D_2$; and
26,27-Dihomo-1,25-Dihydroxy-24-Epi-Vitamin $D_2$ The new analogs were tested in the vitamin D-deficient rat. These tests indicate that 26,27-dihomologation of 1α-hydroxyvitamin $D_2$, 1α-hydroxy-24-epi-vitamin $D_2$ and 1,25-dihydroxy-24-epi-vitamin $D_2$ had a biological activity spectrum that is very different from previously known 26,27-dihomologated 1α,25-dihydroxyvitamin $D_3$ or 22-dehydro-1,25-dihydroxyvitamin $D_3$ compounds. In Tables 1–4 below, representative assay results are given. These include tests of intestinal calcium transport activity (S/M ratios), and of bone mineralization as reflected by serum calcium levels. These assays were conducted according to standard procedures ( see e. g. U.S. Pat. No. 4,588,716) Table 5 illustrates the cell differentiation activity of 26,27-dihomo-24-epi-1α-hydroxyvitamin $D_2$ and 26,27-dihomo-1α-hydroxyvitamin $D_2$ as compared with 26,27-dihomo-24-epi-1,25-dihydroxyvitamin $D_3$. The NBT (nitroblue tetrazolium reduction) and phago (phagocytosis assay) differentiation data of HL-60 cells were obtained from tessts conducted according to standard procedures (see e.g. U.S. Pat. No. 4,973,584).

The data in Table 1 shows that 26,27-dihomo-24-epi-1α,25-dihydroxyvitamin $D_2$ exhibited high activity in stimulating intestinal calcium transport as well as in mobilizing calcium from bone. The activity of this $D_2$ analog is shown to be about the same as for 1,25-dihydroxyvitamin $D_3$.

The data in Tables 2-4 show that the new analog, 26,27-dihomo-1α-hydroxyvitamin $D_2$ and 26,27-dihomo-24-epi-1α-hydroxyvitamin $D_2$ exhibited little or no activity in mobilizing calcium from bone or stimulating intestinal calcium transport. However, as seen in Table 4, the 26,27-dihomo-24-epi-1α-hydroxyvitamin $D_2$ compound decreases bone ash below control values, suggesting that it antagonizes remaining endogenous vitamin D. Similarly, this compound diminishes serum calcium concentration below vitamin D-deficient control values, providing additional evidence that this compound serves as a vitamin D antagonist. These results suggest that this compound could be of considerable importance as an anti-hypercalcemia drug, and can be used in such conditions of neoplastic hypercalcemia, hyperparathyroidism, general hypercalcemia, and vitamin D intoxication hypercalcemia.

The data in Table 5 shows that 26,27-dihomo-1α-hydroxyvitamin $D_2$ has relatively high differentiation activity, i.e. approximately equal to 26,27-dihomo-24-epi-1,25-dihydroxyvitamin $D_3$. In contrast, 26,27-dihomo-24-epi-1α-hydroxyvitamin $D_2$ has little, if any, differentiation activity.

TABLE 1

Response of Vitamin D-Deficient Rats to a Single Dose of 26,27-Dihomo-24-Epi-1α,25-$(OH)_2D_2$

| Group | Amount | Ca Transport (Serosal/Mucosal) | Serum Calcium (mg %) |
|---|---|---|---|
| —D (Control) | 0 | 2.6 ± 0.21 | 4.8 ± 0.11 |
| 1,25-$(OH)_2D_3$ | 50 ng | 3.8 ± 0.44 | 5.5 ± 0.12 |
| | 125 ng | 4.5 ± 0.33 | 5.9 ± 0.15 |
| 26,27-dihomo 24-Epi-1α,25-$(OH)_2D_2$ | 50 ng | 3.8 ± 0.25 | 5.2 ± 0.11 |
| | 125 ng | 4.3 ± 0.21 | 6.0 ± 0.09 |

Each group consisted of 6 rats. Results are mean ±SEN.

Animals were maintained on 0.2% Ca, 3% phosphorus for 3-4 weeks prior to experimentation. Vitamin D compounds were administered in 50 μl of ethanol intrajugularly, and 19 hours later, the rats were killed for determination of serum calcium and intestinal calcium transport.

TABLE 2

Intestinal Calcium Transport and Bone Calcium (Serum Calcium) Mobilization Activities of 26,27-Dihomo-1α-Hydroxyvitamin $D_2$ and 26,27-Dihomo-24-Epi-1α-Hydroxyvitamin $D_2$

| Compound | Dose (pmoles) | Intestinal Ca Transport (S/M Ratio) | Serum Calcium (Bone Ca Mobil.) (mg %) |
|---|---|---|---|
| —D (Control) | 0 | 2.5 ± 3.5 | 3.7 ± 0.20 |
| 1α-OH—$D_2$ | 325 | 5.4 ± 0.37 | 5.3 ± 0.15 |
| 24-Epi-1α-OH—$D_2$ | 325 | 4.3 ± 0.42 | 3.9 ± 0.39 |
| | 650 | 4.4 ± 0.70 | 4.1 ± 0.23 |
| —D (Control) | 0 | 3.4 ± 0.2 | 4.1 ± 0.1 |
| 26,27-Dihomo- 1α-OH—$D_2$ | 100 | 3.6 ± 0.2[b] | 4.6 ± 0.2[b] |
| | 325 | 3.6 ± 0.3[b] | 4.1 ± 0.2[b] |
| 26,27-Dihomo- 1α-OH-24-epi-$D_2$ | 100 | 4.3 ± 0.3[a] | 4.2 ± 0.1[b] |
| | 325 | 4.4 ± 0.3[a] | 4.2 ± 0.1[b] |
| 1α-OH—$D_2$ | 100 | 5.7 ± 0.3[a] | 4.9 ± 0.1[a] |
| | 325 | 5.5 ± 0.2[a] | 5.1 ± 0.07[a] |

[a]Significant difference compared to respective control groups; $p < 0.001$.
[b]No significant difference compared to control.

Rats were fed a 0.02% Ca, 0.3% P diet for 3 weeks and then given the indicated dose (100 pmol) intravenously or (325 pmol) intraperitoneally. The measurements were made 12.5 hours after the dose. There were 6 rats per group.

TABLE 3

Calcium Transport and Bone Calcium Mobilization of Rats Chronically Dosed With 26,27-Dihomo-24-Epi-1α-OH—$D_2$ or 26,27-Dihomo-1α-OH—$D_2$

| Compound | Dose (pmoles/ day) | Ca Transport (S/M) | Serum Calcium (Bone Ca Mobil.) (mg %) |
|---|---|---|---|
| —D (Control) | 0 | 2.7 ± 0.25 | 4.5 ± 0.04 |
| 1α-OH—$D_2$ | 50 | 4.7 ± 0.15 | 5.1 ± 0.22 |
| | 125 | 5.3 ± 0.44 | 5.7 ± 0.07 |
| 26,27-Dihomo- 24-epi-1α-OH—$D_2$ | 50 | — | 3.7 ± 0.13 |
| | 125 | 3.2 ± 0.05 | 4.0 ± 0.30 |
| 26,27-Dihomo- 1α-OH—$D_2$ | 50 | 3.7 ± 0.54 | 4.0 ± 0.18 |
| | 125 | 3.6 ± 0.5 | 3.9 ± 0.18 |

Rats were fed a 0.02% calcium, 0.3% phosphorus vitamin D-deficient diet for 3 weeks and then given the indicated dose intraperitoneally in 0.05 ml of 95% ethanol each day for 7 days. The measurements were made 24 hours after the last dose. There were 6 rats in each group and the data are presented as the mean ±SEM.

TABLE 4

Response of Rachitic Rats to 26,27-Dihomo-1α-OH—$D_2$ And Its 24-Epimer

| Compound | Dose | % Bone Ash | Total mg | Serum P | Line Test |
|---|---|---|---|---|---|
| —D (Control) | 0 | 22 ± 1.0 | 35 ± 1.3 | 2.3 ± 0.4 | 0 |
| 1α-OH—$D_2$ | 12.5 | 24 ± 1.2 | 39 ± 4.0 | 4.0 ± 0.23 | 4.0 ± 0.4 |
| | 25.0 | 26 ± 1.5 | 43 ± 5.0 | 4.7 ± 0.13 | 4.4 ± 0.4 |
| | 50.0 | 26 ± 0.7 | 44.2 ± 1.8 | 4.9 ± 0.22 | 5.4 ± 0.38 |
| 26,27-Dihomo- 24-epi-1α-OH—$D_2$ | 12.5 | 18 ± 0.85 | 28 ± 1.2 | 2.8 ± 0.6 | 0 |
| | 25.0 | 18 ± 1.4 | 28 ± 2.6 | 3.1 ± 0.6 | 0 |
| | 50.0 | 18 ± 2.5 | 31 ± 3.5 | 3.6 ± 0.6 | 0 |
| 26,27-Dihomo- 1α-OH—$D_2$ | 12.5 | 21 ± 1.2 | 35 ± 1.3 | 2.9 ± 0.2 | 0 |
| | 25.0 | 18 ± 1.4 | 29 ± 2.3 | 3.4 ± 0.31 | 0 |
| | 50.0 | 21 ± 0.7 | 35 ± 1.9 | 4.2 ± 0.2 | 0 |

The rats were fed for 3 weeks on a high calcium (1.2%), low phosphorus (0.1%) diet, and then given the indicated dose in 0.05 ml 95% ethanol each day for 7 days. The measurements were made 24 hours after the last dose.

Line nest is degree of mineralization of rachitic epiphyseal plate (see U.S. Pharmacopeia, 1955). Femurs were removed, cleaned and defatted with ethanol for 24 hours and $CHCl_3$ for 24 hours using a Soxhlet extractor.

After dry weight measurement, the bones were ashed in a muffle furnace at 600° F. for 24 hours. The % ash or total ash per femur was recorded. There were 6 rats per group.

TABLE 5

|  | NBT | Phago |
|---|---|---|
| 26,27-Dihomo-24-epi-1,25-(OH)$_2$D$_3$ | | |
| $1 \times 10^{-7}$ | 86 ± 4 | 88 ± 2 |
| $5 \times 10^{-8}$ | 75 ± 3 | 73 ± 2 |
| $1 \times 10^{-8}$ | 62 ± 1 | 63 ± 2 |
| $1 \times 10^{-9}$ | 36 ± 3 | 35 ± 2 |
| 26,27-Dihomo-24-Epi-1α-OH—D$_2$ | | |
| $5 \times 10^{-7}$ | 36 ± 3 | 43 ± 4 |
| $2.5 \times 10^{-7}$ | 12 ± 3 | 13 ± 2 |
| $1 \times 10^{-7}$ | 6 ± 1 | 7 ± 2 |
| $5 \times 10^{-8}$ | 5 ± 2 | 5 |
| $1 \times 10^{-8}$ | 5 ± 1 | 5 |
| 26,27-Dihomo-1α-OH—D$_2$ | | |
| $1 \times 10^{-6}$ | 82 ± 3 | 83 ± 4 |
| $5 \times 10^{-7}$ | 76 ± 2 | 68 ± 4 |
| $1 \times 10^{-7}$ | 61 ± 3 | 57 ± 3 |
| $1 \times 10^{-8}$ | 20 ± 3 | 23 ± 2 |

Thus the preceding assays demonstrate that the new compounds, 26,27-dihomo-1α-hydroxyvitamin D$_2$ and 26,27-dihomo-1α-hydroxy-24-epi-vitamin D$_2$, exhibit a very distinct and unique spectrum of activities. The 26,27-homologated epi-analog actually diminishes percent bone ash and total bone ash, indicating that it is antagonizing any remaining endogenous vitamin D found in the animals. In support of this, the epi-compound diminishes serum calcium below control values in the case of the animals maintained on a low calcium diet. These two lines of evidence demonstrate the antagonistic nature of this compound which is unique in the art. The new 26,27 homologated epi compound, in particular, therefore, represents a valuable addition to the repertoire of useful therapeutic agents, and may be applied advantageously in cases of hypercalcemia of diverse origins.

For treatment purposes, the novel compound of this invention may be formulated as a solution in innocuous solvents, or as an emulsion, suspension or dispersion in suitable solvents or carriers, or as pills, tablets or capsules, together with solid carriers, according to conventional methods known in the art. The compounds are advantageously administered by injection, or by intravenous infusion of suitable sterile solutions, or in the form of liquid or solid doses via the alimentary canal. Doses of from 1 μg to 50 μg per day, particularly of 1α-hydroxy-24-epi-vitamin D$_2$, are appropriate for treatment purposes, such doses being adjusted according to the disease to be treated and the response of the subject as is well understood in the art. Since the new epi compound exhibits specificity of action, it is suitably administered alone, in situations where only calcium transport stimulation is desired, or together with graded doses of another active vitamin D compound—e.g. 1α-hydroxyvitamin D$_2$ or D$_3$, or 1α,25-dihydroxyvitamin D$_3$—in situations where some degree of bone mineral mobilization (together with calcium transport stimulation) is found to be advantageous.

PROCESS SCHEME I

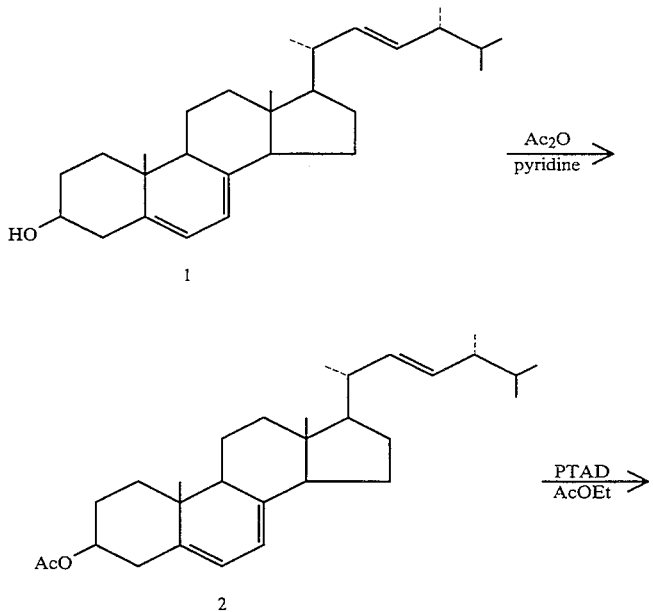

PROCESS SCHEME I
-continued
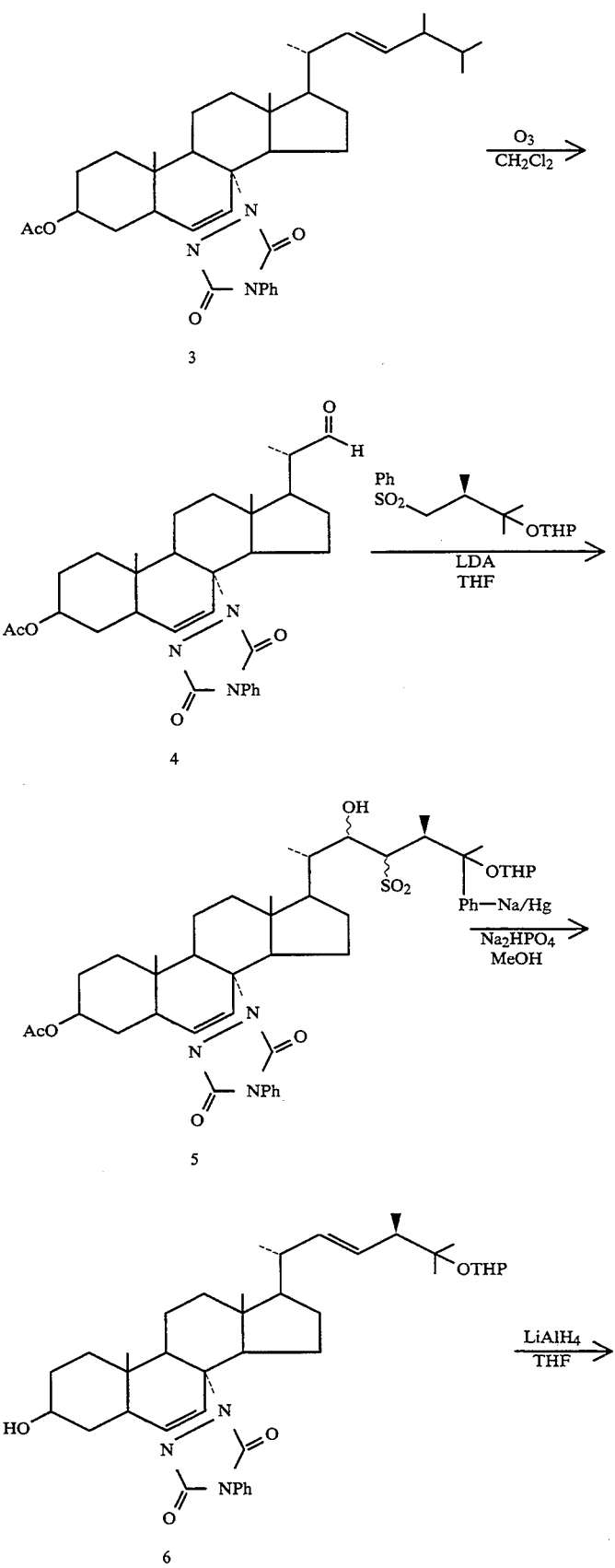

-continued
PROCESS SCHEME I
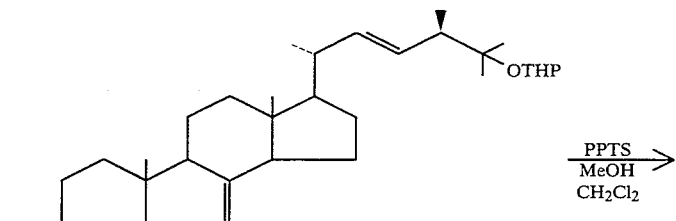
7
PPTS / MeOH / CH₂Cl₂ →
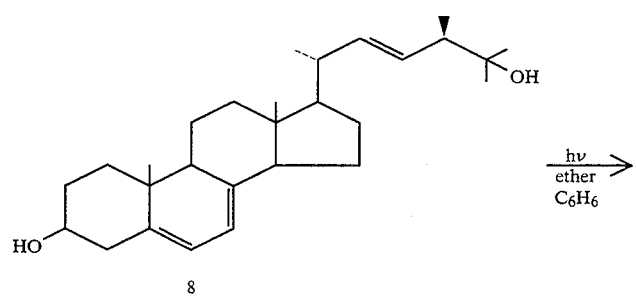
8
hν / ether / C₆H₆ →
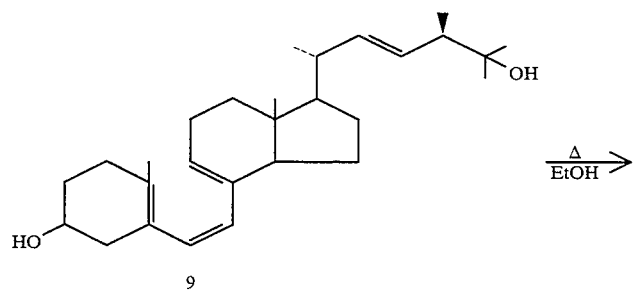
9
Δ / EtOH →
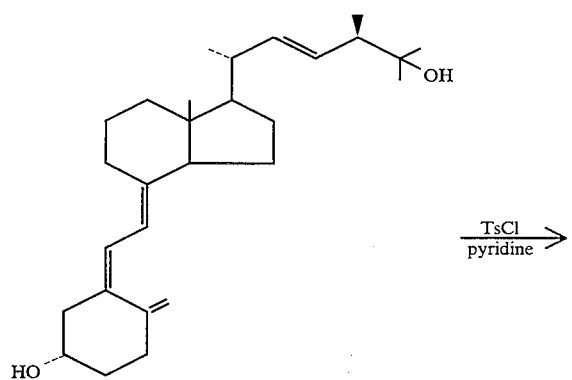
10
TsCl / pyridine →

-continued
PROCESS SCHEME I
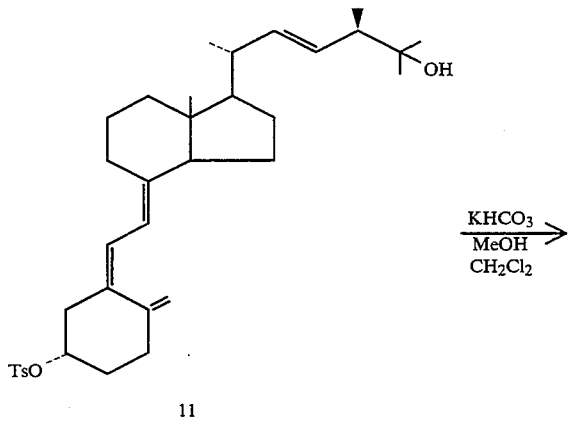
11
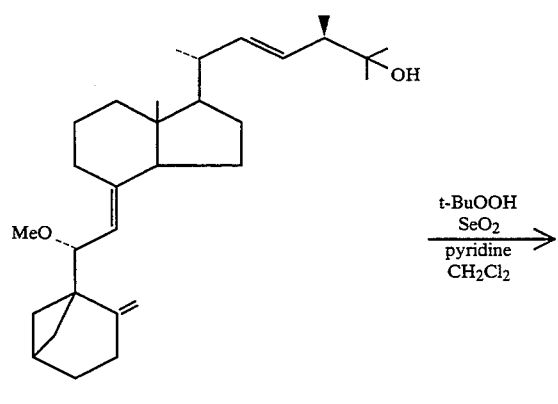
12
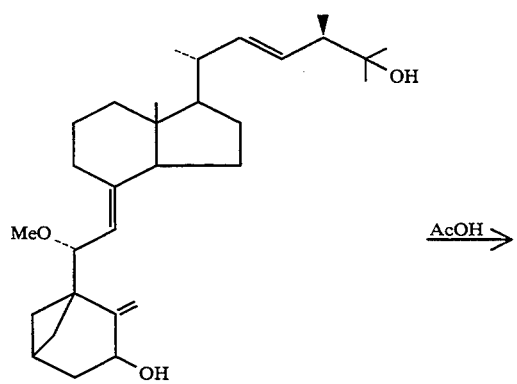
13

PROCESS SCHEME I
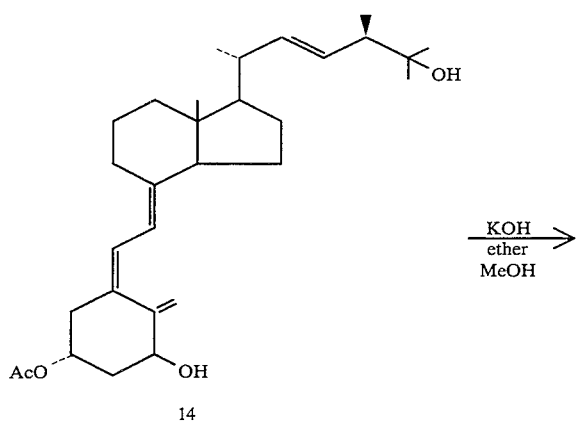
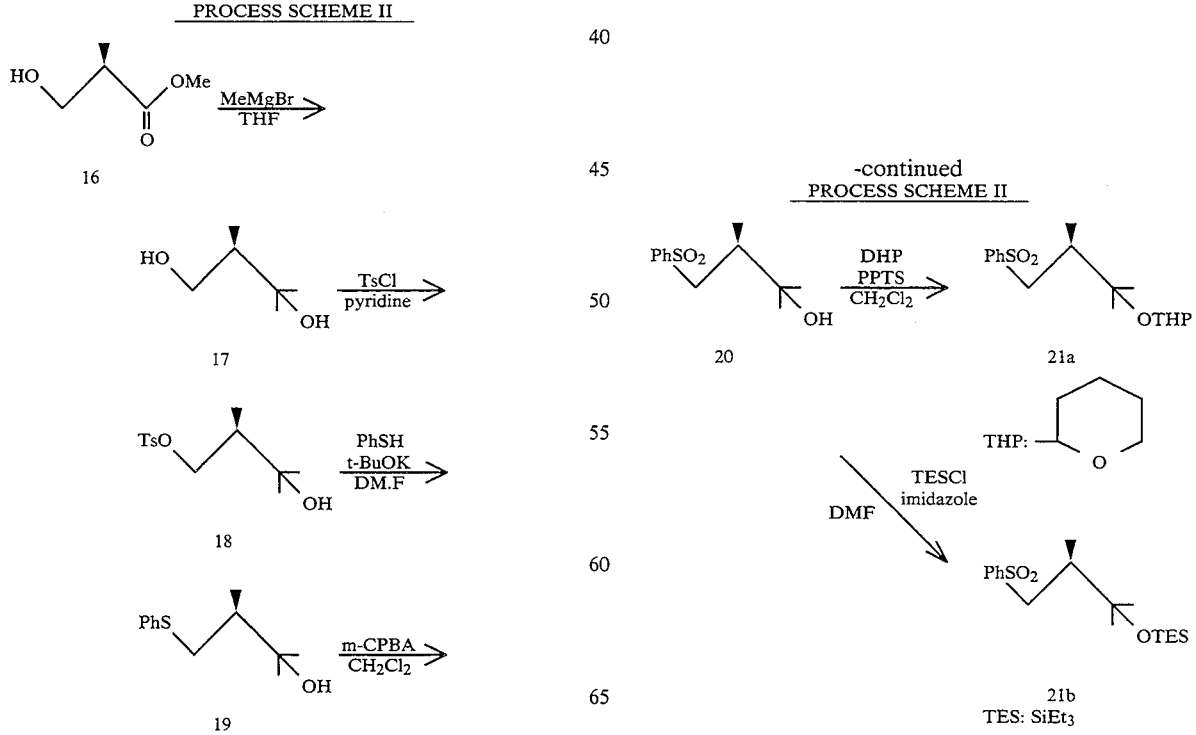

PROCESS SCHEME III
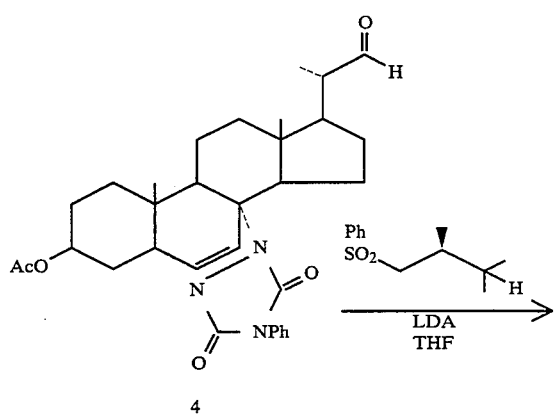
4
Ph SO₂ — / LDA THF →
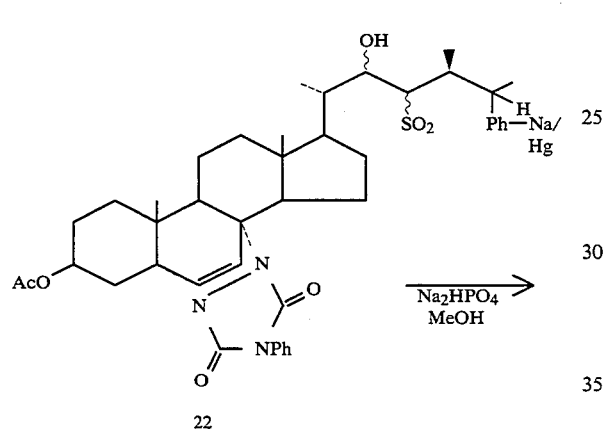
22
Na₂HPO₄ / MeOH →
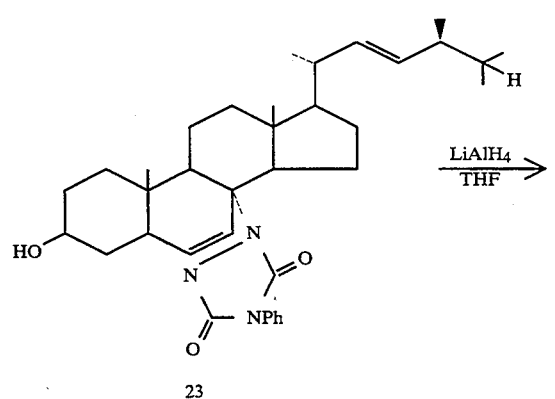
23
LiAlH₄ / THF →
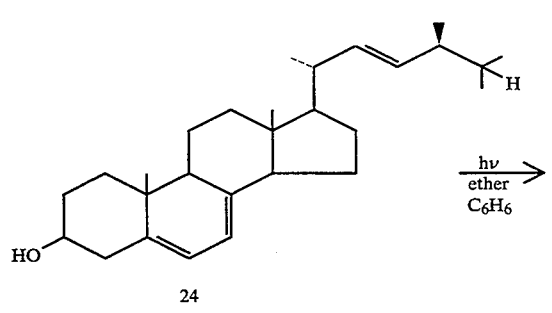
24
hν / ether C₆H₆ →
-continued
PROCESS SCHEME III
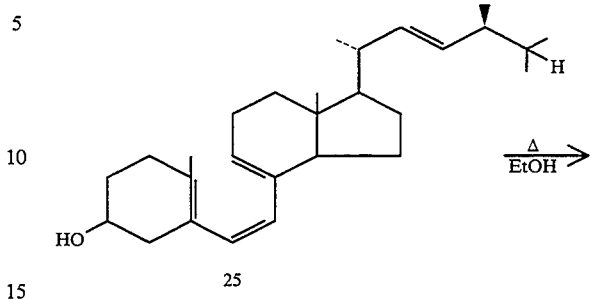
25
Δ / EtOH →
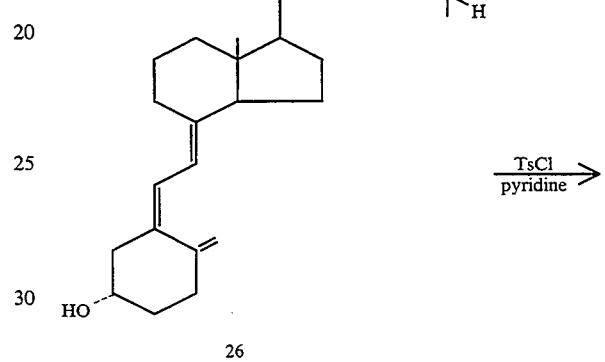
26
TsCl / pyridine →
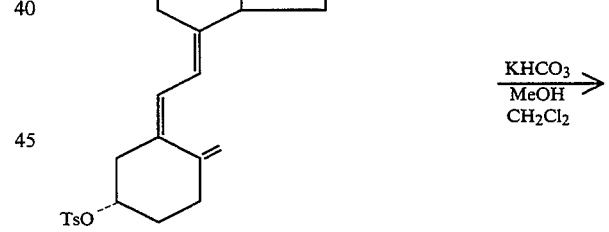
27
KHCO₃ / MeOH / CH₂Cl₂ →
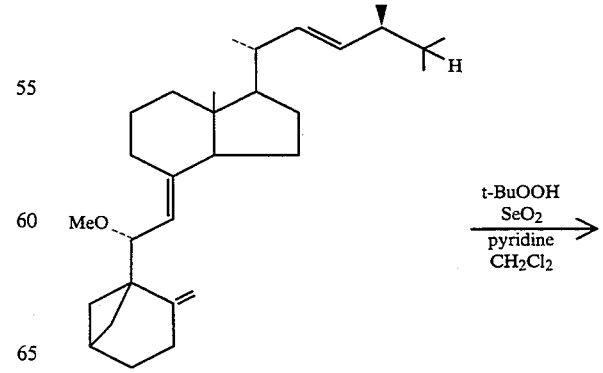
28
t-BuOOH / SeO₂ / pyridine / CH₂Cl₂ →

-continued
PROCESS SCHEME III
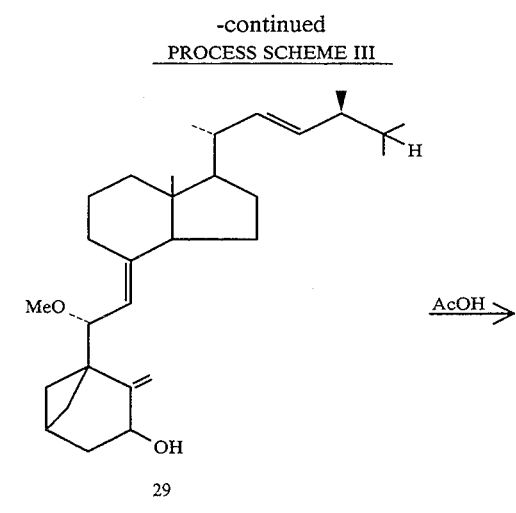
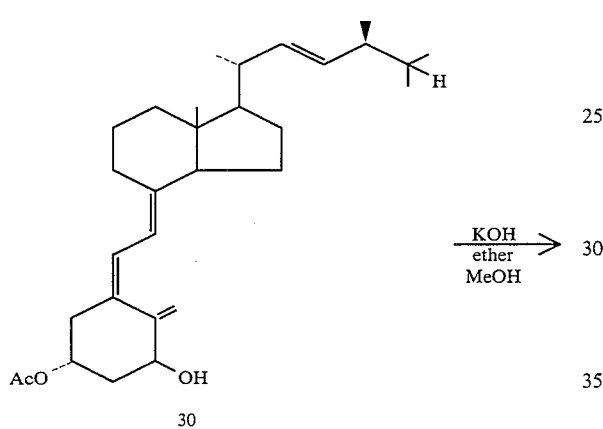
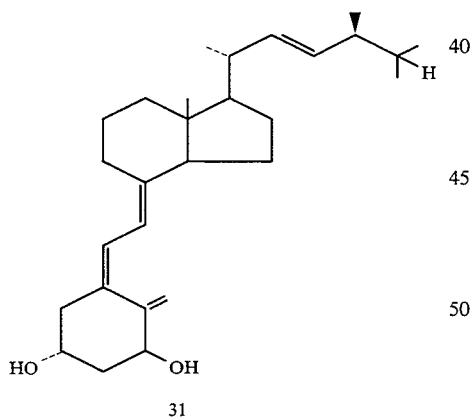
PROCESS SCHEME IV
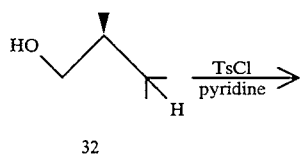
-continued
PROCESS SCHEME IV
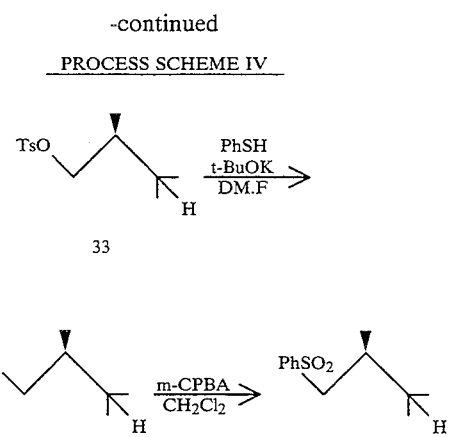
PROCESS SCHEME V
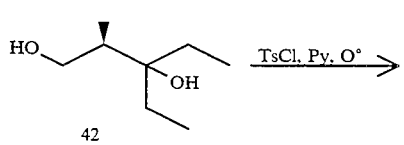
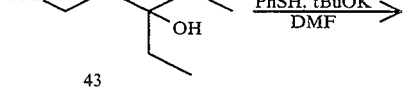
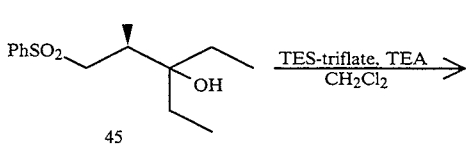
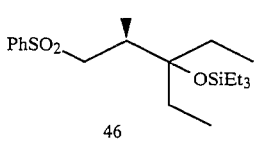

PROCESS SCHEME VI

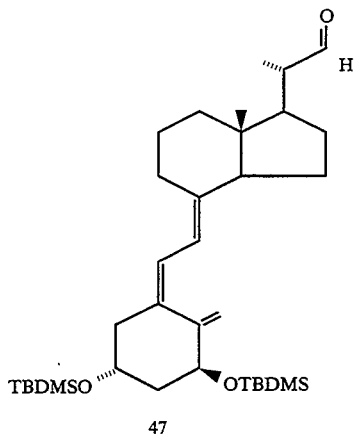
47

+

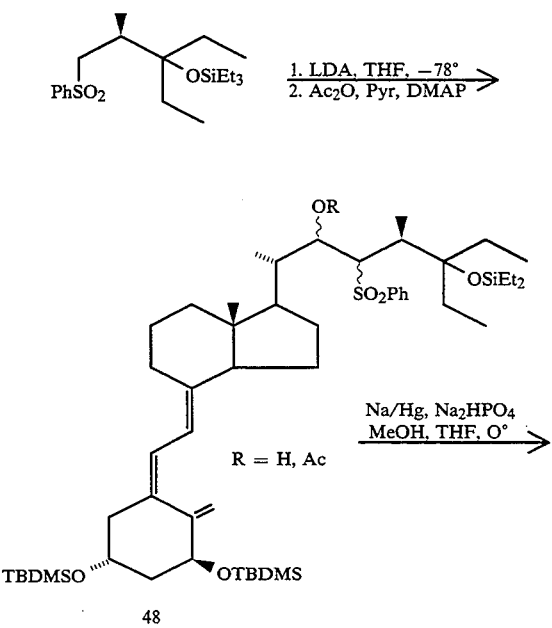
48

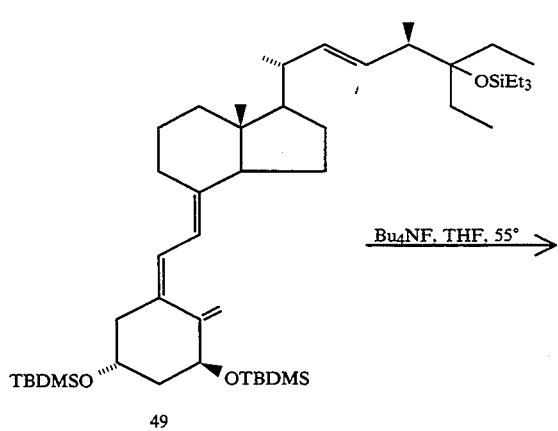
49

-continued
PROCESS SCHEME VI

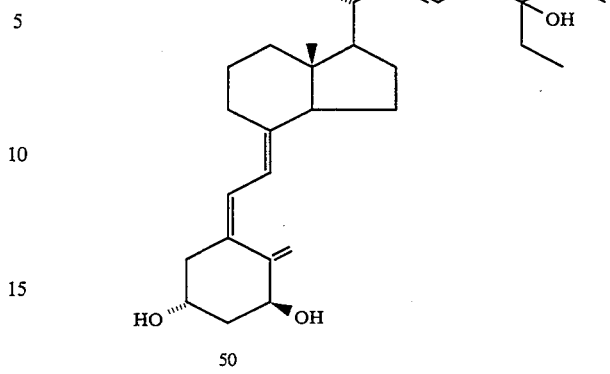
50

We claim:
1. Vitamin D compounds having the formula:

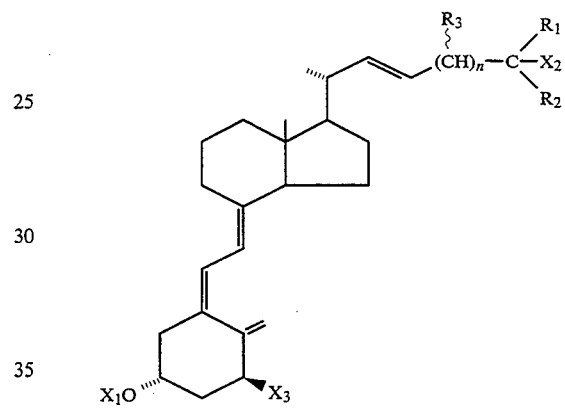

where the configuration about carbon 24 may be R or S and wherein n is an integer having a value of 3, $X_1$ is selected from hydrogen or a hydroxy protecting group, $X_2$ is selected from hydrogen, hydroxy and protected hydroxy, $X_3$ is selected from hydrogen, hydroxy, and protected hydroxy, each $R_3$ is independently selected from alkyl, hydroxy, protected hydroxy, hydrogen or fluorine, with the proviso that at least one $R_3$ must be alkyl, and wherein $R_1$ and $R_2$, which may be the same or different, are each selected from an alkyl or aryl group.
2. The compounds of claim 1 wherein $X_1$ and $X_2$ are both hydrogen, and $X_3$ is hydroxy.
3. The compounds of claim 1 wherein $X_1$ and $X_3$ are both hydrogen, and $X_2$ is hydroxy.
4. The compounds of claim 1 wherein $X_1$ is hydrogen, and $X_2$ and $X_3$ are both hydroxy.
5. 1α,25-dihydroxy-[22E-dehydro-]24-dihomo-vitamin $D_2$ where the configuration about carbon 24 may be R or S having the formula:

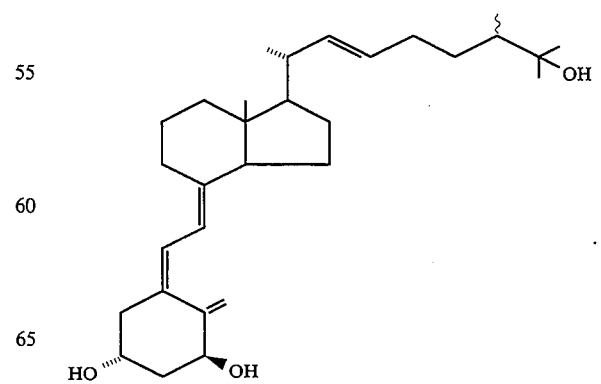

* * * * *